US010590155B2

(12) United States Patent
Kong et al.

(10) Patent No.: US 10,590,155 B2
(45) Date of Patent: Mar. 17, 2020

(54) MITOCHONDRIA-TARGETING FLUORESCENT POTASSIUM+ SENSOR AND METHOD OF MAKING THE SAME

(71) Applicant: ARIZONA BOARD OF REGENTS ON BEHALF OF ARIZONA STATE UNIVERSITY, Scottsdale, AZ (US)

(72) Inventors: Xiangxing Kong, Tempe, AZ (US); Yanqing Tian, Tempe, AZ (US); Fengyu Su, Tempe, AZ (US); Liqiang Zhang, Chandler, AZ (US); Deirdre Meldrum, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/314,753

(22) PCT Filed: Jul. 14, 2017

(86) PCT No.: PCT/US2017/042174
§ 371 (c)(1),
(2) Date: Jan. 2, 2019

(87) PCT Pub. No.: WO2018/013948
PCT Pub. Date: Jan. 18, 2018

(65) Prior Publication Data
US 2019/0153005 A1 May 23, 2019

Related U.S. Application Data

(60) Provisional application No. 62/363,148, filed on Jul. 15, 2016.

(51) Int. Cl.
| | |
|---|---|
| *C07F 9/6596* | (2006.01) |
| *G01N 33/50* | (2006.01) |
| *G01N 33/58* | (2006.01) |
| *G01N 33/68* | (2006.01) |

(52) U.S. Cl.
CPC ....... *C07F 9/6596* (2013.01); *G01N 33/5079* (2013.01); *G01N 33/582* (2013.01); *G01N 33/6872* (2013.01)

(58) Field of Classification Search
CPC  C07F 9/6596; G01N 33/582; G01N 33/6872; G01N 33/5079; C07D 498/18; C07D 498/08; C07D 498/02; A61K 31/69
See application file for complete search history.

(56) References Cited

U.S. PATENT DOCUMENTS

| | | | |
|---|---|---|---|
| 5,134,232 A | 7/1992 | Tsien | |
| 6,211,359 B1 | 4/2001 | He | |
| 8,129,365 B2 | 3/2012 | Verkman | |
| 8,748,192 B2 | 6/2014 | Tian | |
| 9,181,375 B2 * | 11/2015 | Tian | ...................... C07D 498/08 |
| 9,410,970 B2 | 8/2016 | Tian | |
| 10,022,718 B2 | 7/2018 | Martineau | |
| 10,156,573 B2 | 12/2018 | Tian | |
| 2012/0301913 A1 | 11/2012 | Youngbull | |
| 2015/0252061 A1 | 9/2015 | Mazitschek et al. | |
| 2015/0253333 A1 | 9/2015 | Tian | |
| 2016/0202247 A1 | 7/2016 | Tian | |
| 2018/0318835 A1 | 11/2018 | Martineau | |

FOREIGN PATENT DOCUMENTS

| | | |
|---|---|---|
| EP | 0369733 | 5/1990 |
| EP | 1081152 | 3/2001 |
| JP | 2012154693 | 8/2012 |
| WO | 2007044866 | 4/2007 |
| WO | 2012040204 | 3/2012 |
| WO | 2012112440 A2 | 8/2012 |
| WO | 2018136794 A1 | 7/2018 |

OTHER PUBLICATIONS

Kong, X., "A Highly Selective Mitochondria-Targeting Fluorescent K+ Sensor." Angewandte Chemie International Edition 54.41 ( 2015): 12053-12057.*
Kong, X., "A Highly Selective Mitochondria-Targeting Fluorescent K+ Sensor." Angewandte Chemie International Edition 54.41 ( 2015) Supporting Information p. 1-20. anie_201506038_sm_miscellaneous_information.pdf.*
Hirata, T.,"Developnnent of a potassium ion-selective fluorescent sensor based on 3-styrylated BODIPY." Bioorganic & medicinal chemistry letters 21.20 (2011): 6090-6093.*
Zhou, X., "A new highly selective fluorescent K+ sensor." Journal of the American Chemical Society 133.46 (2011): 18530-18533.*
Aguilar-Bryan, L., et al. "Cloning of the beta cell high-affinity sulfonylurea receptor: a regulator of insulin secretion." Science 268.5209 (1995): 423-426.
Baruah, M., et al. "Solvent and pH dependent fluorescent properties of a dimethylaminostyryl borondipyrromethene dye in solution." The Journal of Physical Chemistry A 110.18 (2006): 5998-6009.
Beacham, D. W., et al. "Cell-based potassium ion channel screening using the FluxOR™ Assay." Journal of biomolecular screening 15.4 (2010): 441-446.
Boens, N., et al. "Fluorescent indicators based on BODIPY." Chemical Society Reviews 41.3 (2012): 1130-1172.
Bonnet, S., et al. "A mitochondria-K+ channel axis is suppressed in cancer and its normalization promotes apoptosis and inhibits cancer growth." Cancer cell 11.1 (2007): 37-51.
Carpenter RD, et al. Synthesis of a Sensitive and Selective Potassium-Sensing Fluoroionophore. Organic Letters. 2010;12(6):1160-3.

(Continued)

*Primary Examiner* — John M Mauro
(74) *Attorney, Agent, or Firm* — Quarles & Brady LLP; Jessica L. Lewis

(57) ABSTRACT

Mitochondria-targeting potassium sensors and method(s) for making such sensors. The sensor shows a response to potassium and displays a 130-fold dynamic range of fluorescence intensity and high brightness. The sensors response to potassium concentrations was demonstrated to be unaffected by cellular pH value and/or concentrations of other ions. The sensors can be used for monitoring the mitochondrial potassium efflux/influx.

9 Claims, 20 Drawing Sheets

(56) References Cited

OTHER PUBLICATIONS

Carpenter, R. D., et al. "Function-oriented synthesis of a didesmethyl triazacryptand analogue for fluorescent potassium ion sensing." European journal of organic chemistry 2011.7 (2011): 1242-1248.
Chalmers, S., et al. "The mitochondrial membrane potential and Ca2+ oscillations in smooth muscle." Journal of cell science 121.1 (2008): 75-85.
Dunn, K. W., et al. "A practical guide to evaluating colocalization in biological microscopy." American Journal of Physiology-Cell Physiology 300.4 (2011): C723-C742.
Feldmann, Reliability of Scientific Data, Journal of Pharmaceutical Science, 66, 2 (1977).
Garlid, K. D., et al. "Mitochondrial potassium transport: the K+ cycle." Biochimica et Biophysica Acta (BBA)—Bioenergetics 1606. 1-3 (2003): 23-41.
He, H., et al. "A fluorescent sensor with high selectivity and sensitivity for potassium in water." Journal of the American Chemical Society 125.6 (2003): 1468-1469.
Hirata, T., et al. "Development of a potassium ion-selective fluorescent sensor based on 3-styrylated BODIPY." Bioorganic & medicinal chemistry letters 21.20 (2011): 6090-6093.
Hopfer, U., et al. "Protonic conductance across phospholipid bilayer membranes induced by uncoupling agents for oxidative phosphorylation." Proceedings of the National Academy of Sciences of the United States of America 59.2 (1968): 484.
Hu, Q., et al. "Mitochondria-Targeted Cancer Therapy Using a Light-Up Probe with Aggregation-Induced-Emission Characteristics." Angewandte Chemie International Edition53.51 (2014): 14225-14229.
Huang, X., et al. "Targeting potassium channels in cancer." J Cell Biol 206.2 (2014): 151-162.
International Search Report and Written Opinion for PCT/US2017/042174, dated Sep. 29, 2017.
Jackson, D. G., et al. "ATP and potassium ions: a deadly combination for astrocytes." Scientific reports 4 (2014): 4576.
Jiang, S., et al. "Formation and Rupture of a Supramolecular Nanocapsule Triggered on-off-on Supramolecular Switch for Zn2+." European Journal of Organic Chemistry 2013.13 (2013): 2591-2596.
Karstens, T., et al. "Rhodamine B and rhodamine 101 as reference substances for fluorescence quantum yield measurements." The journal of physical chemistry 84.14 (1980): 1871-1872.
Kofuji, P, et al, "Potassium buffering in the central nervous system." Neuroscience 2004, 129, 1045-1056.
Kong, X., et al. "A Highly Selective Mitochondria-Targeting Fluorescent K+ Sensor." Angewandte Chemie International Edition 54.41 (2015): 12053-12057.
Krumova, K., et al. "Fluorogenic a-tocopherol analogue for monitoring the antioxidant status within the inner mitochondrial membrane of live cells." Journal of the American Chemical Society 135.45 (2013): 17135-17143.
Leung, C. W. T., et al. "A photostable AIE luminogen for specific mitochondrial imaging and tracking." Journal of the American Chemical Society 135.1 (2012): 62-65.
Levin, M., et al. "Regulation of cell behavior and tissue patterning by bioelectrical signals: challenges and opportunities for biomedical engineering." Annual review of biomedical engineering 14 (2012): 295-323.
Lidstrom, M. E., et al. "Life-on-a-chip." Nature Reviews Microbiology 1.2 (2003): 158.
Magzoub, M., et al. "Millisecond association kinetics of K+ with triazacryptand-based K+ indicators measured by fluorescence correlation spectroscopy." The journal of physical chemistry B 110.42 (2006): 21216-21221.
Malinska, D., et al. "Mitochondrial potassium channels and reactive oxygen species." FEBS letters 584.10 (2010): 2043-2048.
Mattson, M. P., et al. "Mitochondria in cell death: novel targets for neuroprotection and cardioprotection." Trends in molecular medicine 9.5 (2003): 196-205.

McManus, O. B. "HTS assays for developing the molecular pharmacology of ion channels." Current opinion in pharmacology 15 (2014): 91-96.
Miller, C. "An overview of the potassium channel family." Genome biology 1.4 (2000): reviews0004-1.
Minta, A., et al. "Fluorescent indicators for cytosolic sodium." Journal of Biological Chemistry 264.32 (1989): 19449-19457.
Muñoz-Planillo, R., et al. "K+ efflux is the common trigger of NLRP3 inflammasome activation by bacterial toxins and particulate matter." Immunity 38.6 (2013): 1142-1153.
Namkung W, et al. Cell-Based Fluorescence Screen for K+ Channels and Transporters Using an Extracellular Triazacryptand-Based K+ Sensor. Journal of the American Chemical Society. 2008;130(25):7794-5.
Namkung W, et al. In Situ Measurement of Airway Surface Liquid [K+] Using a Ratioable K+-sensitive Fluorescent Dye. Journal of Biological Chemistry. 2009;284(23):15916-26.
Nolin, F., et al. "Changes to cellular water and element content induced by nucleolar stress: investigation by a cryo-correlative nano-imaging approach." Cellular and molecular life sciences 70.13 (2013): 2383-2394.
Padmawar P, et al. K+ waves in brain cortex visualized using a long-wavelength K+-sensing fluorescent indicator. Nature Methods. 2005;2(11):825-7.
Perry, S. W., et al. "Mitochondrial membrane potential probes and the proton gradient: a practical usage guide." Biotechniques 50.2 (2011): 98-115.
Petrilli, V., et al. "Activation of the NALP3 inflammasome is triggered by low intracellular potassium concentration." Cell death and differentiation 14.9 (2007): 1583.
Remington's Pharmaceutical Sciences, 17th ed., Mack Publishing Company, Easton, Pa., 1985, p. 1418.
Rezazadeh, S., et al. "Rb+ flux through hERG channels affects the potency of channel blocking drugs: correlation with data obtained using a high-throughput Rb+ efflux assay." Journal of biomolecular screening 9.7 (2004): 588-597.
Rorsman, P., et al. "Regulation of insulin secretion in human pancreatic islets." Annual review of physiology 75 (2013):155-179.
Ross, M. F., et al. "Lipophilic triphenylphosphonium cations as tools in mitochondrial bioenergetics and free radical biology." Biochemistry (Moscow) 70.2 (2005): 222-230.
Rurack, K., et al. "Molecular switching in the near infrared (NIR) with a functionalized boron—dipyrromethene dye." Angewandte Chemie International Edition 40.2 (2001): 385-387.
Shim, S.-H., et al. "Super-resolution fluorescence imaging of organelles in live cells with photoswitchable membrane probes." Proceedings of the National Academy of Sciences 109.35 (2012): 13978-13983.
Shimizu, S., et al. "Bcl-2 prevents apoptotic mitochondrial dysfunction by regulating proton flux." Proceedings of the National Academy of Sciences 95.4 (1998): 1455-1459.
Szabo, I., et al. "Mitochondrial channels: ion fluxes and more." Physiological reviews 94.2 (2014): 519-608.
Szabò, I., et al. "Physiology of potassium channels in the inner membrane of mitochondria." Pflügers Archiv-European Journal of Physiology 463.2 (2012): 231-246.
Szmacinski, H., et al. "Potassium and sodium measurements at clinical concentrations using phase-modulation fluorometry." Sensors and Actuators B: Chemical 60.1 (1999): 8-18.
Urrego, D., et al. "Potassium channels in cell cycle and cell proliferation." Philosophical Transactions of the Royal Society B: Biological Sciences 369.1638 (2014): 20130094.
Wang, Z.-W., et al. "SLO-1 potassium channels control quantal content of neurotransmitter release at the C. elegans neuromuscular junction." Neuron 32.5 (2001): 867-881.
Wojtovich, A. P., et al. "A novel mitochondrial KATP channel assay." Circulation research 106.7 (2010): 1190.
Wulff, H., et al. "K+ channel modulators for the treatment of neurological disorders and autoimmune diseases." Chemical reviews 108.5 (2008): 1744-1773.
Xu, J., et al. "The voltage-gated potassium channel Kv1. 3 regulates peripheral insulin sensitivity." Proceedings of the National Academy of Sciences 101.9 (2004): 3112-3117.

(56) References Cited

OTHER PUBLICATIONS

Zhou, X., et al. "A new highly selective fluorescent K+ sensor." Journal of the American Chemical Society 133.46 (2011): 18530-18533.

Zhou, X., et al. "Triazacryptand-based fluorescent sensors for extracellular and intracellular K+ sensing." Biomaterials 32.33 (2011): 8574-8581.

U.S. Appl. No. 16/479,373, filed Jul. 19, 2019, titled Fluorescent pH Sensors and Methods of Preparing and Using Them, first named inventor Liqiang Zhang.

* cited by examiner

FIG. 4A  FIG. 4B  FIG. 4C
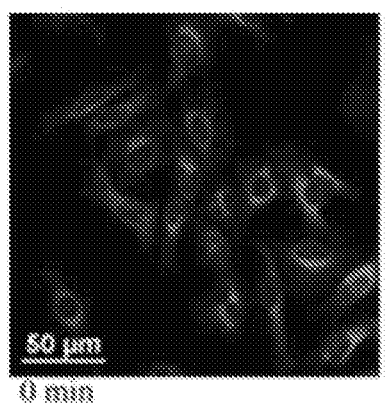 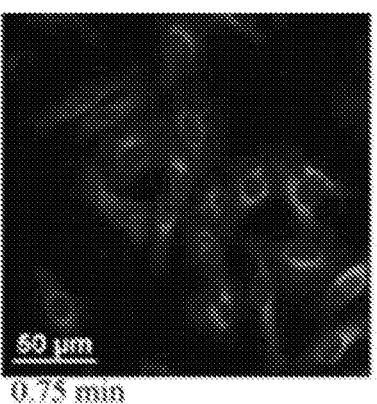 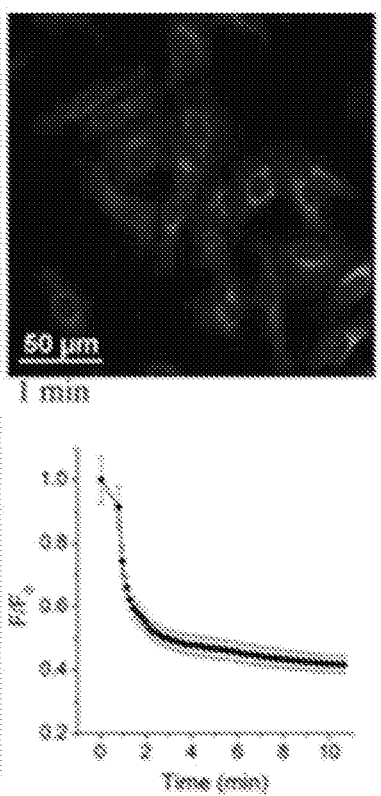
FIG. 4D  FIG. 4E  FIG. 4F FIG. 5A
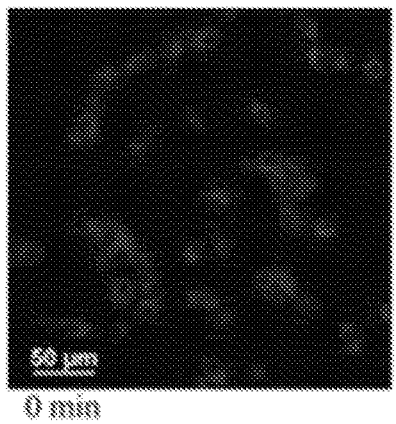
FIG. 5B
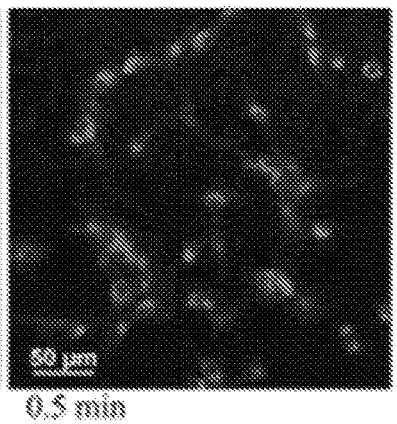
FIG. 5C
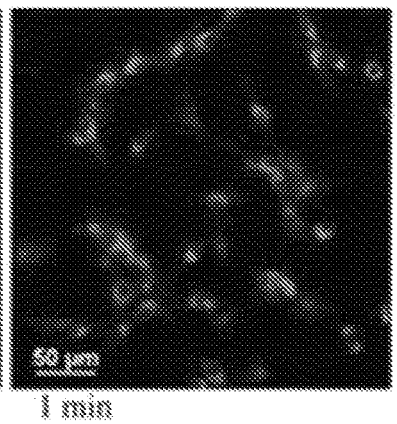
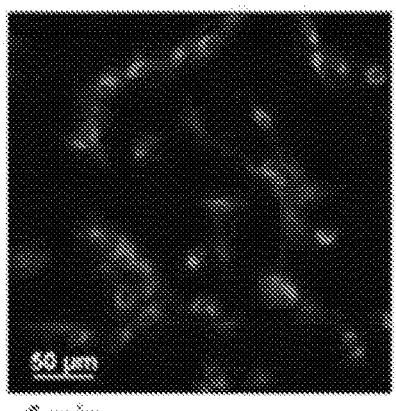
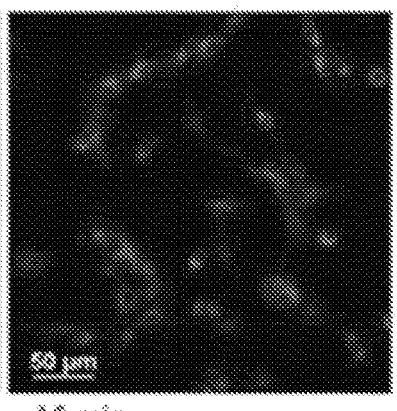
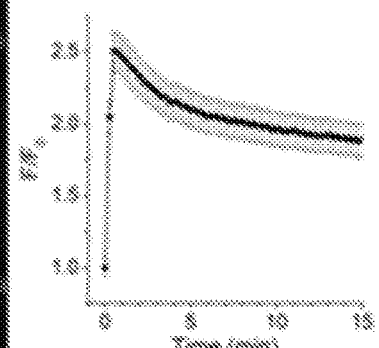
FIG. 5D
FIG. 5E
FIG. 5F

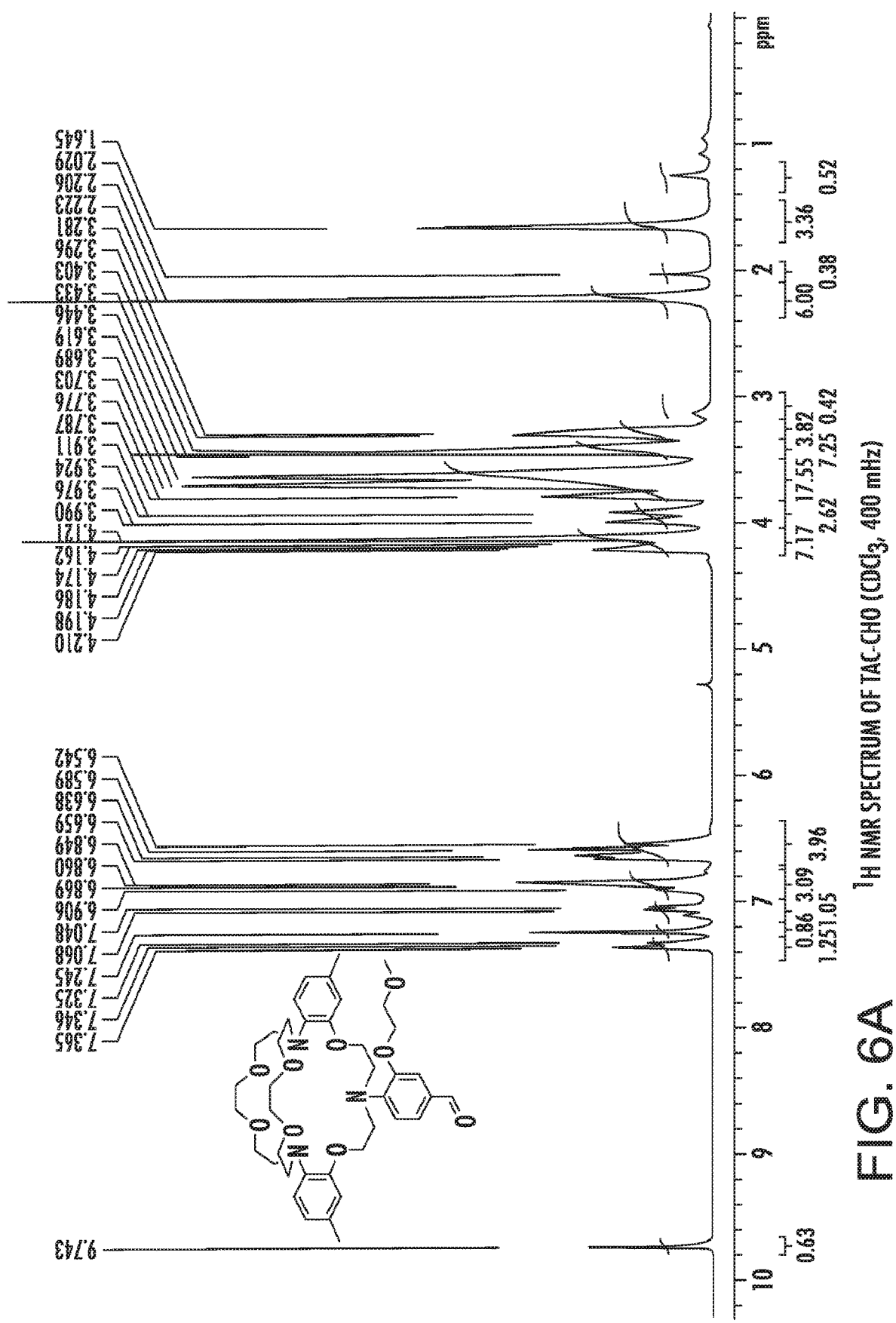

MITOCHONDRIA-TARGETING FLUORESCENT POTASSIUM+ SENSOR AND METHOD OF MAKING THE SAME

CROSS-REFERENCE TO RELATED APPLICATIONS

This application represents the national stage entry of PCT International Application No. PCT/US2017/042174, filed on Jul. 14, 2017, and claims priority from the U.S. Provisional Patent Application No. 62/363,148 filed on Jul. 15, 2016, the disclosures of which are incorporated herein by reference.

STATEMENT REGARDING FEDERALLY SPONSORED RESEARCH OR DEVELOPMENT

This invention was made with government support under P50 HG002360 and U01 CA164250 awarded by the National Institutes of Health. The government has certain rights in the invention.

BACKGROUND

Potassium channels (KCh) belong to a class of transmembrane proteins with more than 100 genes coding for the principle subunits. KCh are involved in many physiological functions, such as cell proliferation, growth, apoptosis, reactive oxygen species creation, inflammasome formation, and insulin secretion. By opening or blocking KCh and thus adjusting the potassium-ion concentration in cellular organelles, a cell can control cell-membrane potential, contribute to cardiac action potentials and neurotransmitter release, and affect various critical biological functions. It has been recently determined that KCh is a potential pharmacological target in treating cancer, autoimmune disease, neuroprotection, cardioprotection, and diabetes.

Typical research tools for KCh study include a patch-clamp technique, a fluxOR™ assay method using $Tl^+$ ion and corresponding fluorescent probes, and a $Rb^+$ ion method. While these methods have been demonstrated to be useful for high-throughput screening of drugs with a certain type of potassium channels, related art is limited in understanding of the relationship(s) in a multi-factor pathway in the cell. Due to the lack of fluorescent potassium sensors targeting mitochondria, most research on mitochondrial KCh uses indirect experimental methods, leaving lots of uncertainty in the research conclusion.

Recent research demonstrated that $K^+$ flux through the inner mitochondrial membrane had a significant effect in insulin secretion, inflammasome formation, and cell apoptosis. Development of a mitochondria-targeting $K^+$ sensor is critical in investigation of the potassium-related mitochondrial signaling processes and the pathway of the disease, including single cell metabolic analysis, cancer studies, and new drug screening.

SUMMARY

Embodiments of the present disclosure provide a potassium-sensing compound, interchangeably referred to as a potassium sensor, and methods for forming one embodiment of said compound. This potassium-sensing compound is highly selective for monitoring potassium ($K^+$) ion dynamics in mitochondria. The disclosed potassium sensor is characterized by sensing a range of the potassium concentration between about 30 mM and about 500 mM. In a specific implementation, when this potassium sensor is exposed to potassium concentrations, it demonstrates a large, a 130-fold dynamic range in response (at a $K^+$ concentration of 0.8 M). Additionally, the fluorescence intensity of said potassium sensor increases 1.3 fold at a wavelength of light of about 572 nm when said compound is exposed to a concentration of potassium at about 5 mM and increases 57 fold at a wavelength of light of about 572 nm when said compound is exposed to a concentration of potassium at about 150 mM.

In certain embodiments, the mitochondria-targeting potassium sensor is insensitive to cellular pH values and/or concentrations (mM) of ions of other metal that are typical in normal and healthy cells. The potassium sensor produces fluorescence intensity that is independent from a cellular pH value within a range from about 5.5 to about 9. In certain embodiments, the potassium sensor produces fluorescence intensity independent from intracellular concentration of other ions, such as, $Na^+$, $Ca^{2+}$, $Mg^{2+}$, $Fe^{3+}$, $Fe^{2+}$, $Zn^{2+}$, $Mn^{2+}$, and $Cu^{2+}$, at a concentration from about 50 μM to about 15 mM.

Embodiments of a method for producing one embodiment of the mitochondria-targeting potassium sensor include a step of reacting between 4-(6-Bromohexyloxy)-benzaldehyde and triphenylphosphine to obtain a first solid; a step of reacting the first solid and 2,4-dimethylpyrrole in dichloromethane in the presence of catalytic trifluoroacetic acid; optionally followed by oxidation with p-chloranil (or 2,3-Dichloro-5,6-dicyano-p-benzoquinone, DDQ), triethylamine, and boron trifluoride diethyl etherate ($BF_3OEt_2$), as well as a step of purification with the use of silica chromatography to obtain a second solid. An embodiment may further include refluxing the so-procured second solid with TAC-CHO in a benzene, by using piperidine-acetic acid as catalyst, followed by purification with the use of silica chromatography to obtain the sensor.

BRIEF DESCRIPTION OF DRAWINGS

The idea of the present technology is better understood with reference to the following generally not-to-scale Drawings, of which:

FIG. 3A illustrates red emission from KS6; FIG. 3B provides a representation of green emission from MitoTracker® Green; and FIG. 3C shows an overlay of MitoTracker Green, KS6 and bright-field images;

FIGS. 4A, 4B, 4C, 4D, and 4E shows time-dependent fluorescence images of KS6-stained HeLa cells stimulated by ionomycin observed under confocal fluorescence microscope: t=0 (before the addition of ionomycin); t=0.75, 1, 2, 10 min, respectively, after adding ionomycin (20 μM final concentration) into the culture medium containing 20 mM of KCl. FIG. 4F shows the average fluorescence intensity ratios as measured by Image J. $F_0$ is the average fluorescence intensity at t=0 min; F is the average fluorescence intensity at other times;

FIGS. 5A, 5B, 5C, 5D, and 5E presents time-dependent fluorescence images of KS6-stained U87MG cells stimulated by nigericin observed under confocal fluorescence microscope: t=0 (before the addition of nigericin); t=0.5, 1, 5, 15 min, respectively, after adding nigericin (20 μM final concentration) into the culture medium containing 200 mM of KCl; FIG. 5F shows the average fluorescence intensity ratios as measured by Image J.

FIG. 6A illustrates an $^1$H NMR spectrum of TAC-CHO in $CDCl_3$;

DESCRIPTION

Figure 1A:
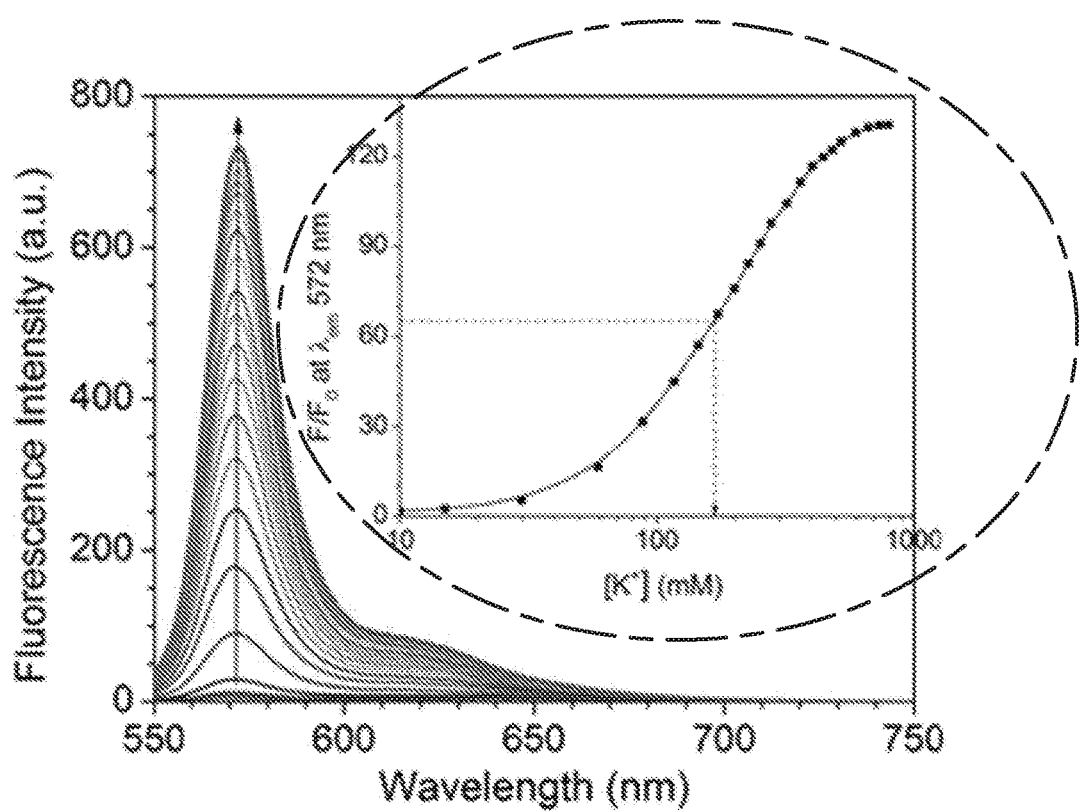
FIG. 1A presents fluorescence spectra of KS6 (5.0 μM) in Tris buffer (pH=7.4, 5 mM)/CTAB (0.50 mM) with different KCl concentrations, ($\lambda_{ex}$: 540 nm)

Embodiments of the technology solve the issue of monitoring potassium ion levels in mitochondria of a living cell by providing a mitochondria-targeting potassium sensor.

This technology is described with examples referring to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology. Thus, appearances of the phrases "in one embodiment," "in an embodiment," and similar language throughout this specification may, but do not necessarily, all refer to the same embodiment.

The described features, structures, or characteristics of the embodiments may be combined in any suitable manner in one or more embodiments. In the following description, numerous specific details are recited to provide a thorough understanding of the embodiments. One skilled in the relevant art will recognize, however, that the technology may be practiced without one or more of the specific details, or with other methods, components, materials, and so forth. In other instances, well-known structures, materials, or operations are not shown or described in detail to avoid obscuring aspects of the technology.

For the terms "for example" and "such as," and grammatical equivalents thereof, the phrase "and without limitation" is understood to follow unless explicitly stated otherwise. As used herein, the term "about," when used in combination with a specific numerical value representing a physical characteristic, is defined to account for and include a variation or deviation from such numerical value that is typically encountered in related art when performing a measurement of the physical characteristic in question with the use of a described technique. Numerical result of any measurement disclosed below is understood to be modified by the term "about," whether or not the term is explicitly used and unless explicitly stated otherwise.

The term "salt" refers to any ionic form of a compound and one or more counter-ionic species (cations and/or anions). The term "salt" additionally includes zwitterionic compounds (i.e., a molecule containing one more cationic and anionic species, e.g., zwitterionic amino acids). Counter ions present in a salt can include any cationic, anionic, or zwitterionic species. Examples of anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, trifluoromethanesulfonate, ethanesulfonate, benzenesulfonate, p-toluenesulfonate, p-trifluoromethyl benzenesulfonate, hydroxide, aluminates and borates. Examples of cations include, but are not limited to: monovalent alkali, metal cations, such as lithium, sodium, potassium, and cesium, and divalent alkaline earth metals, such as beryllium, magnesium, calcium, strontium, and barium. Also covered by this term are transition metal cations, such as gold, silver, copper and zinc, as well as non-metal cations, such as ammonium salts.

The term "pharmaceutically acceptable" is used to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The scope of the present technology also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present technology include the conventional non-toxic salts of the parent compound formed, for example, from non-toxic inorganic or organic acids. The pharmaceutically acceptable salts of the present technology can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, isopropanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. Conventional methods for preparing salt forms are described, for example, in *Handbook of Pharmaceutical Salts: Properties, Selection, and Use,* Wiley-VCH, 2002.

The compounds described below, including salts of such compounds, can be prepared using known organic synthesis techniques and can be synthesized according to any of numerous possible synthetic routes.

With respect to a mitochondria-targeting $K^+$ sensor, in certain embodiments, the sensor comprises a formula I:

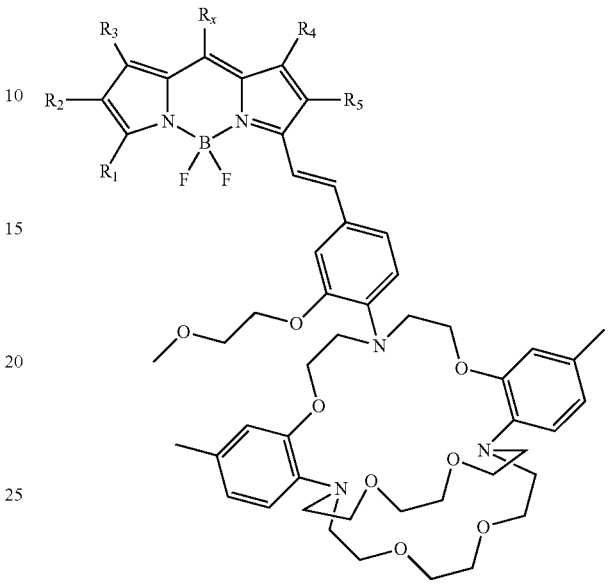

(I)

or a salt form thereof.

In certain embodiments, a mitochondria-targeting moiety, $R_x$, which is independently selected from the group consisting of

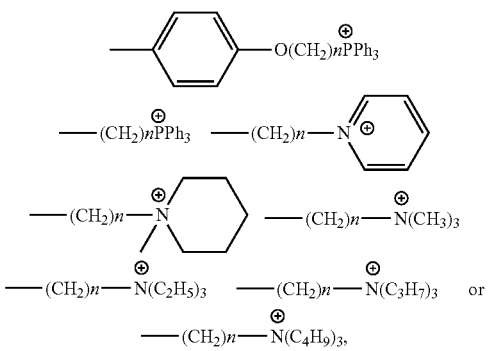

wherein n is greater than about 1 and less than about 20.

Further, $R_1$, $R_3$, $R_4$ in formula (I) are independently selected from the group consisting of H, $CH_3$, $CH_2CH_3$; and $R_2$, $R_5$ in formula (I) are independently selected from the group consisting of H, $CH_3$, $CH_2CH_3$, $CO_2H$, $CO_2CH_3$, $CO_2Et$, $CH_2CH_2COOCH_3$, $CH_2CH_2COOCH_2CH_3$, $CH_2CH_2COOH$, and 2-thiophene.

In certain embodiments, the mitochondria-targeting $K^+$ sensor is generated, by attaching a mitochondria-targeting moiety to a fluorophore, which is compatible with a chosen mitochondria-targeting moiety and contains $K^+$ binding ligand triazacryptand (TAC). In some embodiments, a lipophilic triphenylphosphonium cation ($TPP^+$) is used as the mitochondria-targeting moiety. In some embodiments, 3-styrylated boron-dipyrromethene (BODIPY) is used as the mitochondria-targeting moiety compatible fluorophore (M. F. Ross, G. F. Kelso, F. H. Blaikie, A. M. James, H. M.

Cocheme, A. Filipovska, T. Da Ros, T. R. Hurd, R. A. J. Smith, M. P. Murphy, *Biochemistry—Moscow* 2005, 70, 222-230; Q. L. Hu, M. Gao, G. X. Feng, B. Liu, *Angew. Chem. Int. Ed.* 2014, 53, 14225-14229; K. Krumova, L. E. Greene, G. Cosa, *J. Am. Chem. Soc.* 2013, 135, 17135-17143; C. W. T. Leung, Y. N. Hong, S. J. Chen, E. G. Zhao, J. W. Y. Lam, B. Z. Tang, *J. Am. Chem. Soc.* 2013, 135, 62-65).

The term "fluorophore" or "fluorophore moiety" as used herein, by itself or as part of another group, means a molecule or a portion of a molecule which exhibits fluorescence (K. Rurack, M. Kollmannsberger, J. Daub, *Angew. Chem. Int. Ed.* 2001, 40, 385-387; M. Baruah, W. W. Qin, C. Flors, J. Hofkens, R. A. L. Vallee, D. Beljonne, M. Van der Auweraer, W. M. De Borggraeve, N. Boens, *J. Phys. Chem. A* 2006, 110, 5998-6009). In certain embodiments, a mitochondria-targeting moiety compatible fluorophore can be utilized to synthesize different embodiments of mitochondria-targeting K+ sensors, which can be described with the following non-limiting formulae:

Formula 4

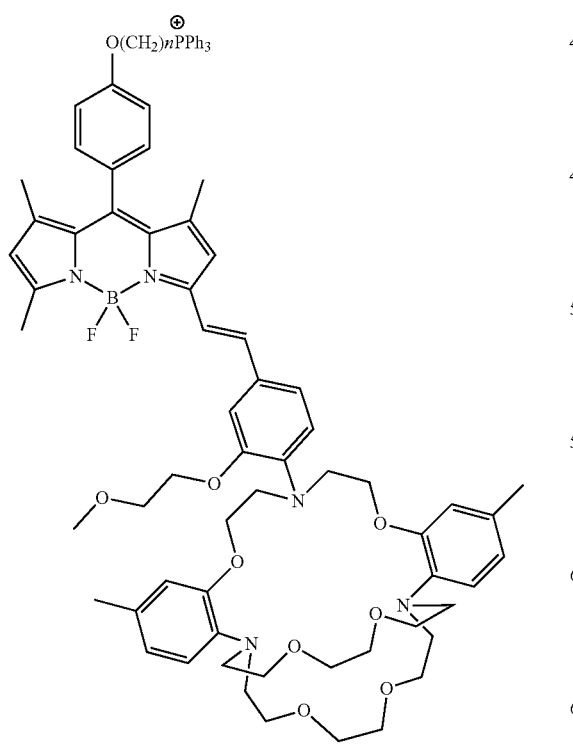

Formula 5

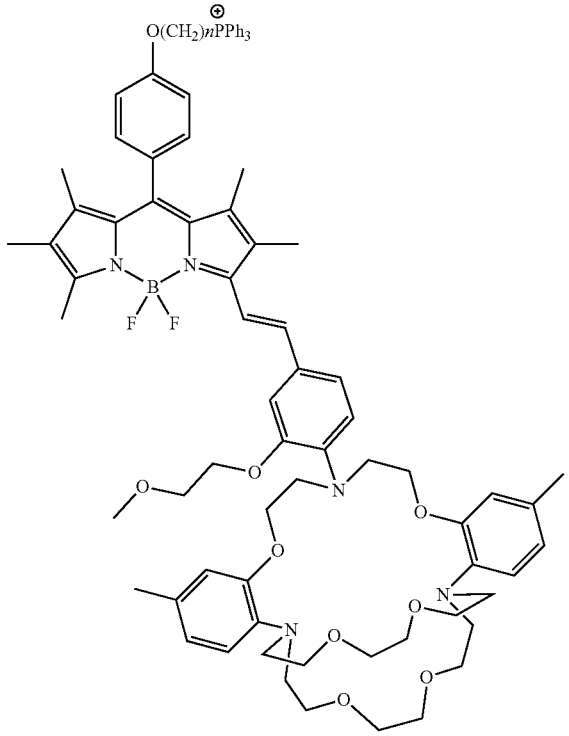

Formula 6

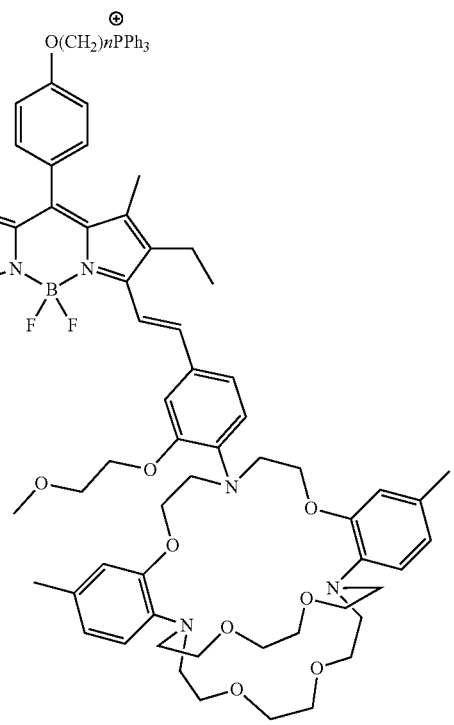

Formula 7
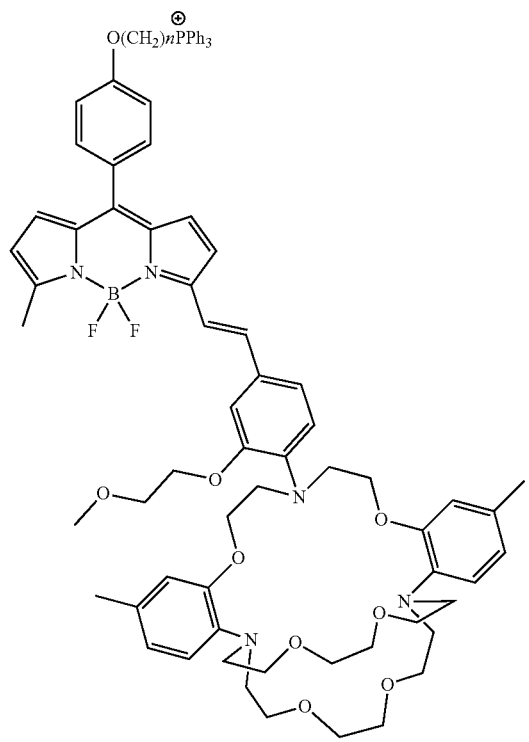
Formula 8
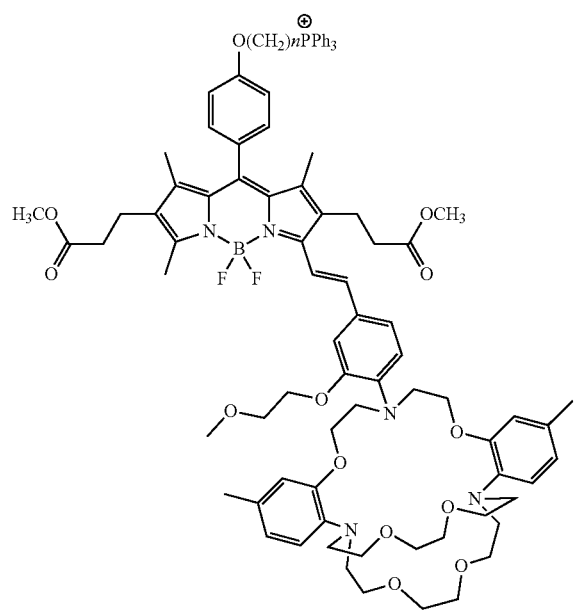
Formula 9
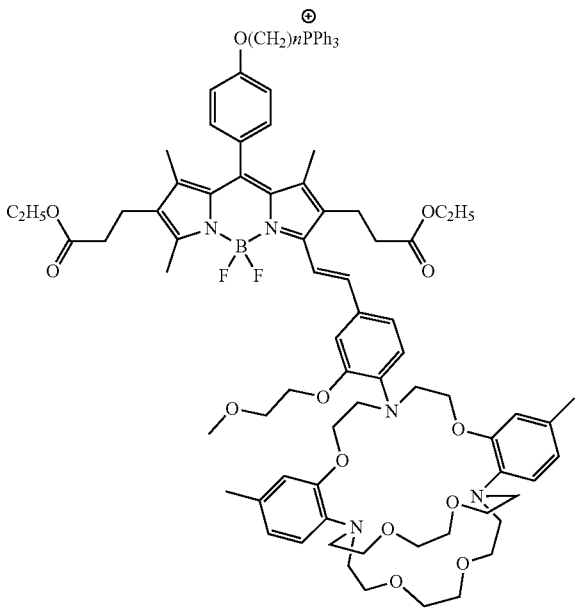
Formula 10
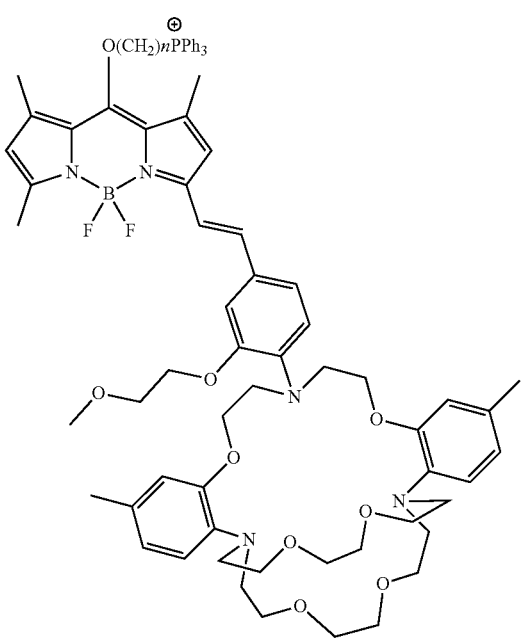

Formula 11
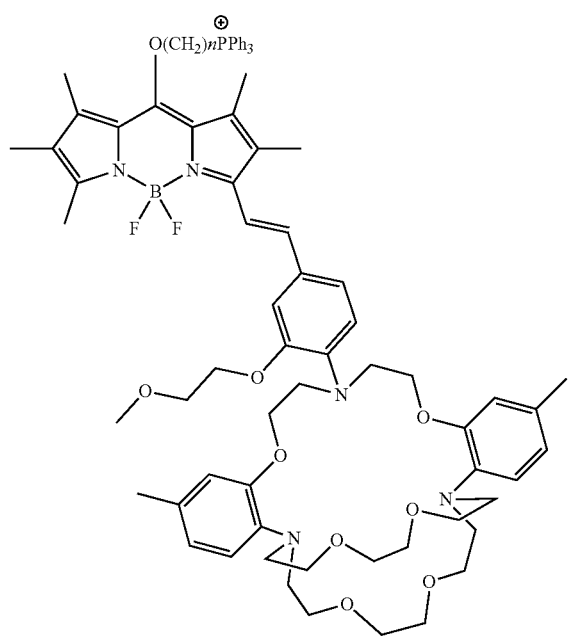
Formula 13
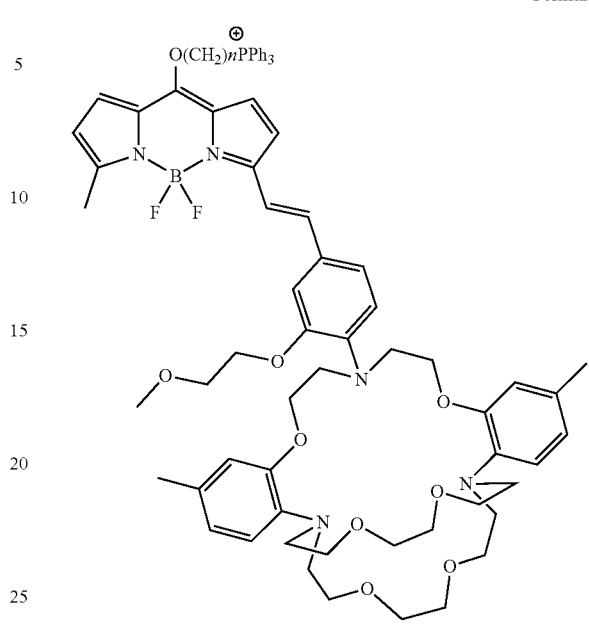
Formula 12
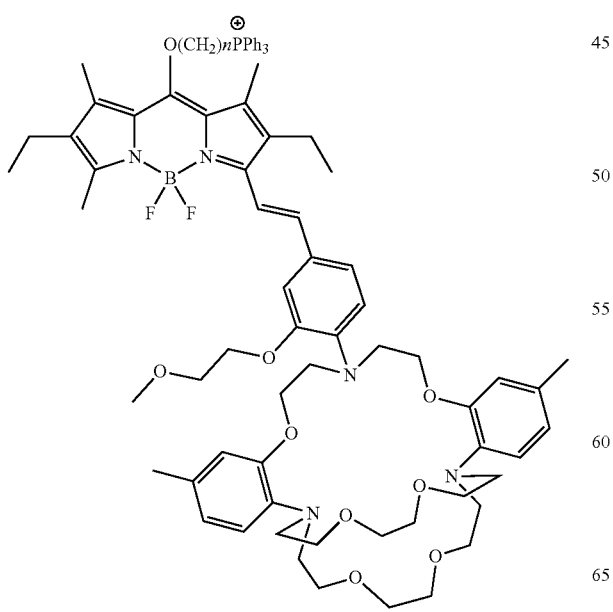
Formula 14
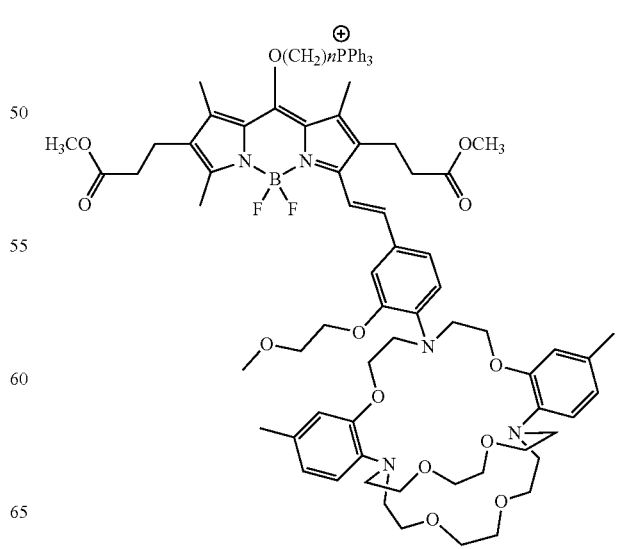

Formula 15

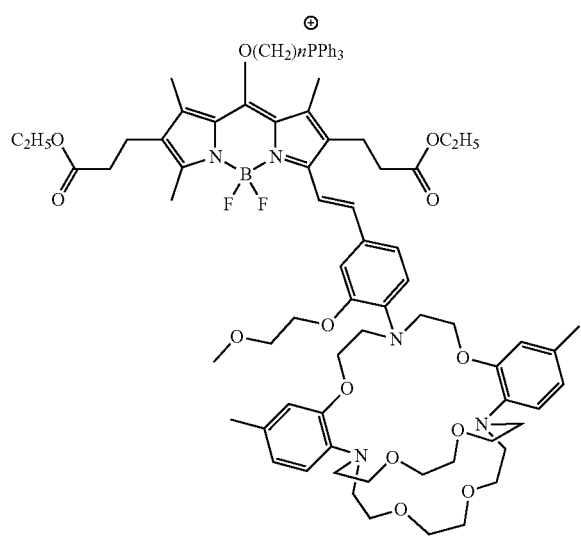

In one embodiment of the current disclosure, the mitochondria-targeting potassium sensor (referred to as a KS6 sensor) has a structure comprising formula II:

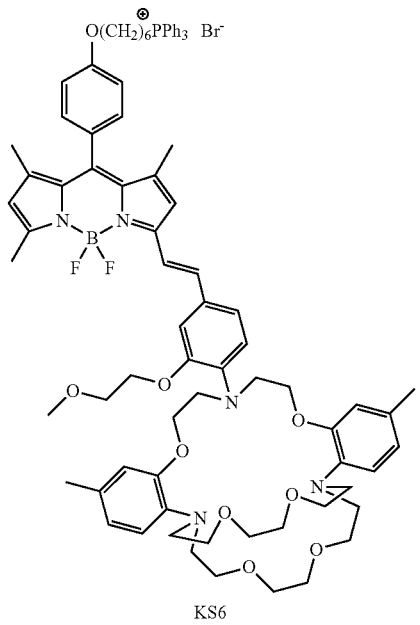

KS6

The structure of the KS6 is characterized by mass spectrometry, such as H NMR and MALDI-TOF-mass spectra, and any other mass spectrometry technologies known to a person having ordinary skill in the art. In certain embodiments, KS6 is soluble in organic solvents, such as DMSO, $CH_2Cl_2$, chloroform, or any organic solvent known to a person having ordinary skill in the art. In certain embodiments, KS6 is insoluble in water.

Figure 1B:
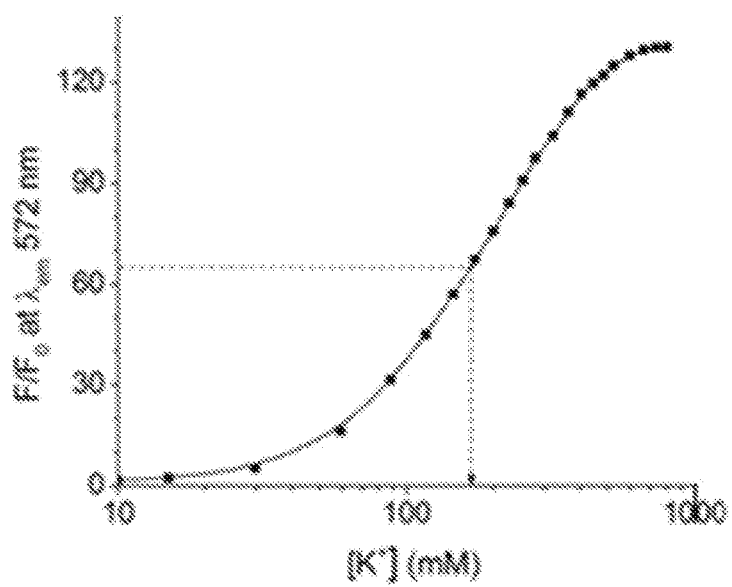
FIG. 1B shows a plot of normalized intensity $F/F_0$ at 572 nm as a function of $[K^+]$. $F_0$ is the intensity before adding $K^+$ ions. F is defined as the intensity determined at various concentrations of $K^+$ ions.

Referring to FIGS. 1A and 1B, the titration of KS6 is carried out in aqueous solutions that do not contain any organic solvent. In certain embodiments, KS6 solution, dissolved in DMSO, is dispersed in Tris/HCl buffer (pH about 7.4) containing cetrimonium bromide (CTAB) with the surfactant concentrations below their critical micelle concentrations. The concentrations of KS6-DMSO solution and the Tris/HCl buffer vary according to different experiment conditions. In certain embodiments, the final concentration of KS6 in the aqueous Tris/HCl-CTAB solution is about 5 μM.

Figure 7B:
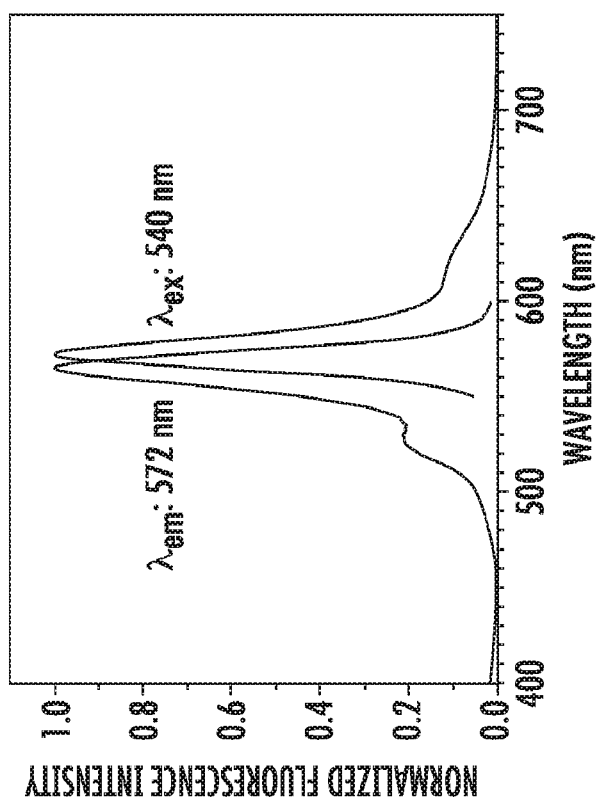
FIG. 7B shows excitation and emission spectra of KS6 in Tris buffer (pH=7.4; 5.0 mM)/CTAB (0.5 mM) solution containing 0.80 M KCl.
Figure 7A:
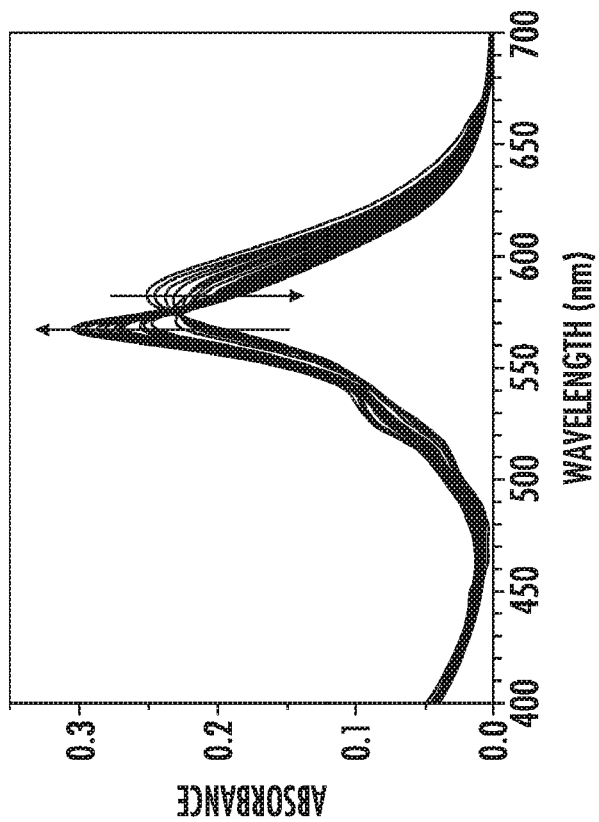
FIG. 7A provides UV-Vis absorption spectra of KS6 during the titration in Tris buffer (pH=7.4; 5.0 mM)/CTAB (0.5 mM) solution from 0 mM to 0.80 M $K^+$.

Further, referring to FIGS. 1A and 7A, in certain embodiments, the potassium concentration is within the range from about 5 to 800 mM and the emission spectrum of KS6-$K^+$ complex demonstrated a maximum peak at 572 nm and a broad shoulder peak from 600 to 690 nm. Without binding any $K^+$, in certain embodiments, KS6 has a maximum absorbance peak at 582 nm in aqueous solution and an extinction coefficient of $2.5 \times 10^4$ $M^{-1}cm^{-1}$ (FIG. 7A). The extent to which a sample absorbs light depends upon the wavelength of light. The wavelength at which a substance shows maximum absorbance is called absorption maximum or Amax. In other embodiments, upon binding $K^+$ (0.8 M), the maximum absorbance peak blue-shifted to 567 nm with an extinction coefficient of $3.05 \times 10^4$ $M^{-1}cm^{-1}$. Further, KS6 demonstrated very weak fluorescence peak in its free form at 572 nm, and a quantum yield ($\phi_f$) as low as 0.7% using rhodamine 101 in ethanol ($\phi_f$=1.0) as a standard. In one example, when the extracellular concentration of $K^+$ is about 5 mM, the fluorescence peak at 572 nm was empirically measured to increase about 1.3 fold, which corresponded to $\phi_f$ of 1.0%; and when the intracellular concentration of $K^+$ was about 150 mM, in another example, the fluorescence peak at 572 nm was increases about 57 fold, which corresponded to $\phi_f$ of 14.4%.

Referring to FIG. 1B, KS6 is shown to be suitable for monitoring r within a range between 30 mM and 500 mM, based on the normalized values of intensities $F/F_0$ as a function of $K^+$. Here, $F_0$ is the intensity before adding r ions and F is the intensity at various concentrations of $K^+$ ions.

Figure 2A:
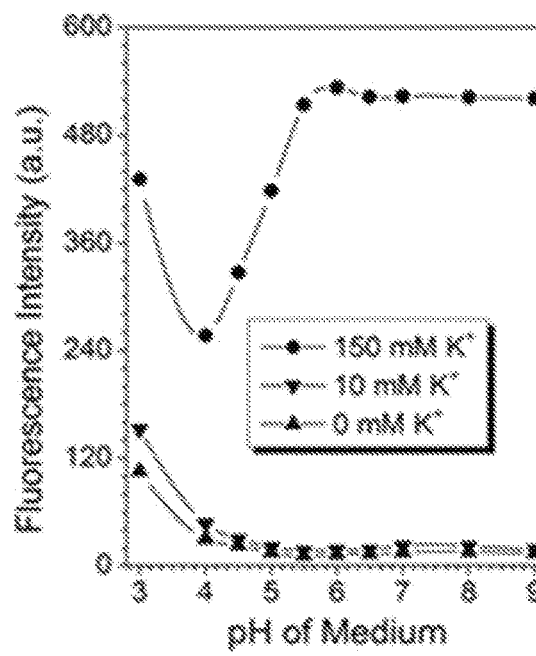
FIG. 2A shows the plots of fluorescence intensities of KS6 (5 μM) in different pH Britton-Robinson buffer solution (CTAB: 0.5 mM) containing no KCl, 10 mM KCl, and 150 mM KCl, respectively.

Referring to FIG. 2A, in certain embodiments, KS6 sensor of the invention is demonstrated to be independent of pH of the aqueous buffer solution in the range from about 5.5 to about 9.0, which evidences the suitability of KS6 sensors, configured to an embodiment, for targeting mitochondria (because the pH value in mitochondria is around 8 and more than likely does not decreases below 5.5). "About" as used herein is to describe a difference of plus or minus 10% with respect to a stated value.

Figure 2B:
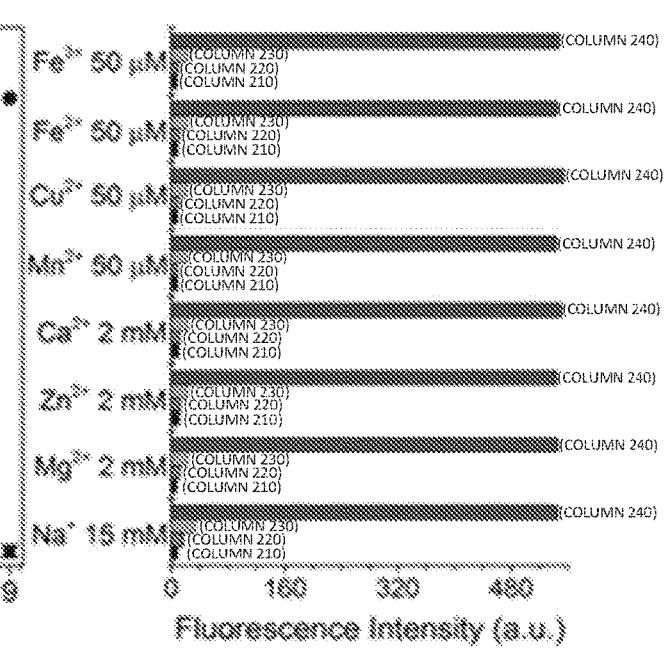
FIG. 2B Fluorescence intensities of KS6 (5 μM KS6 in CTAB: 0.5 mM) containing only sensor (column 210), adding metal ions (column 220), adding both metal ions and 5 mM KCl (column 230), and metal ions and 150 mM KCl (column 240)

Referring to FIG. 2B, in certain embodiments, KS6 sensors demonstrated selectivity towards potassium ions and chemical stability to $H_2O_2$, indicating its capability to monitor the concentration change of $K^+$ in intracellular environments. For example, in the presence of 100 mM $H_2O_2$, the fluorescence intensity of the KS6 sensors does not change. Fluorescence intensity of a KS6 sensor of the disclosure did not change when the KS6 sensor was exposed to physiological concentrations mimicking intracellular environment of $Na^+$, $Ca^{2+}$, $Mg^{2+}$, $Fe^{3+}$, $Fe^{2+}$, $Zn^{2+}$, $Mn^{2+}$, and $Cu^{2+}$. KS6 sensor was exposed to $H_2O_2$ (100 mM) and no fluorescence intensity change was observed.

Figure 8B:
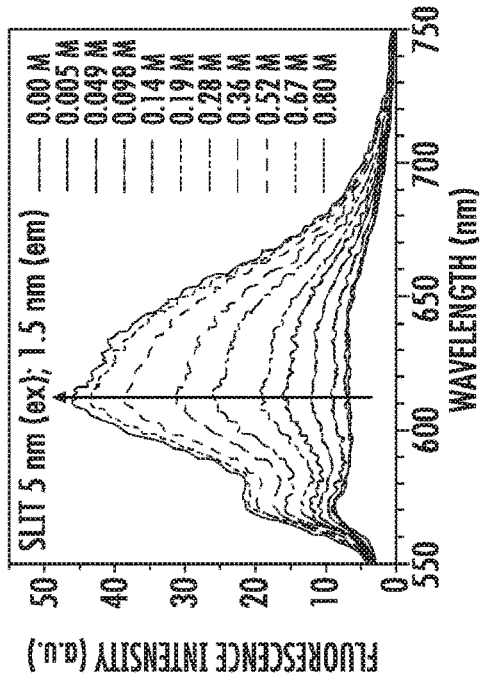
FIG. 8B shows fluorescence spectra of KS6 during the titration in Tris/HCl buffer (pH=7.4; 5.0 mM)/CTAB (0.5 mM) solution from 0.00 M to 0.80 M $Na^+$.
Figure 8C:
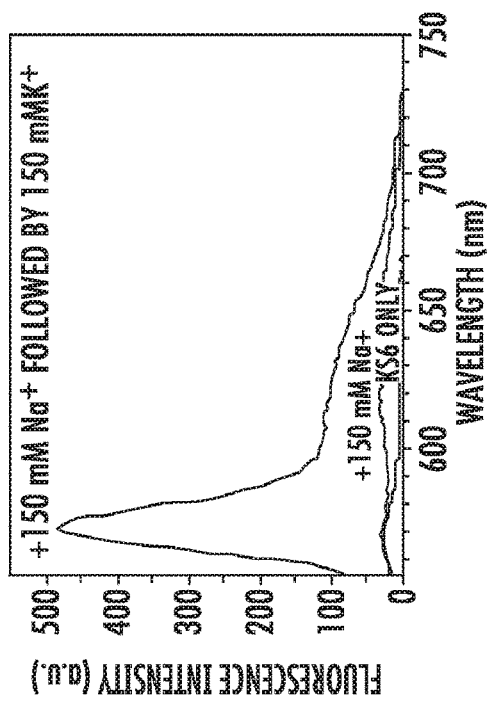
FIG. 8C provides fluorescence spectra of KS6 in Tris/HCL buffer (pH=7.4; 5.0 mM)/CTAB (0.5 mM) solution, after adding in $Na^+$ to make that the final concentration of $Na^+$ is 150 mM; and followed by adding in $K^+$ to make the final $K^+$ and $Na^+$ are 150 mM.
Figure 8A:
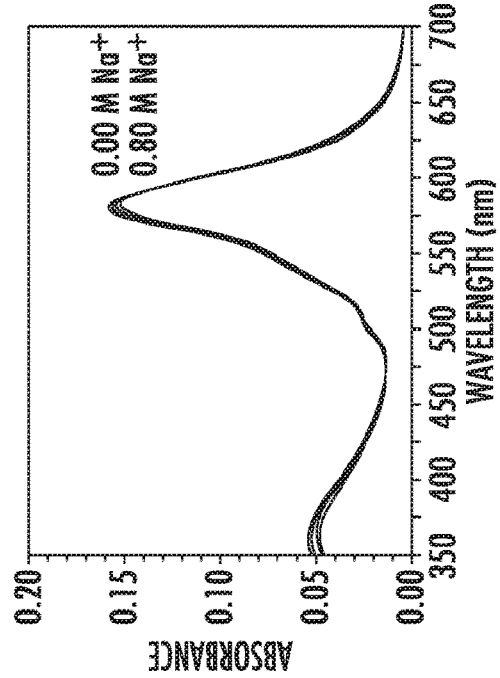
FIG. 8A shows UV-Vis spectra of KS6 during the titration in Tris/HCl buffer (pH=7.4; 5.0 mM)/CTAB (0.5 mM) solution from 0.00 M to 0.80 M $Na^+$.

Referring to FIGS. 8A, 8B, and 8C, the sensing mechanism of the KS6 sensor was further tested and ruled out BODIPY fluorophores's changes in fluorescence are not caused by changes of the polarity of the solvent in the aqueous buffer solution. In certain embodiments, a NaCl aqueous solution (4.0 M) was used to titrate the KS6 sensor for comparison. Unlike in the case of titration with KCl, no UV-Vis spectra change was observed during the titration with NaCl (FIG. 8A). The fluorescence band in the range of 600-700 nm increased with the increase of the concentration of Na+ up to 0.80 M (FIG. 8B). At a Na+ concentration of about 150 mM, which is close to the extracellular concentration of Na+ the increase of fluorescence intensity caused by the ionic strength effect can be omitted (FIG. 8C), indicating that the response of KS6 was mainly due to the binding to the potassium ions, and not its dispersion in less polar CTAB phase at a high ionic strength.

Figures 3A, 3B, 3C:
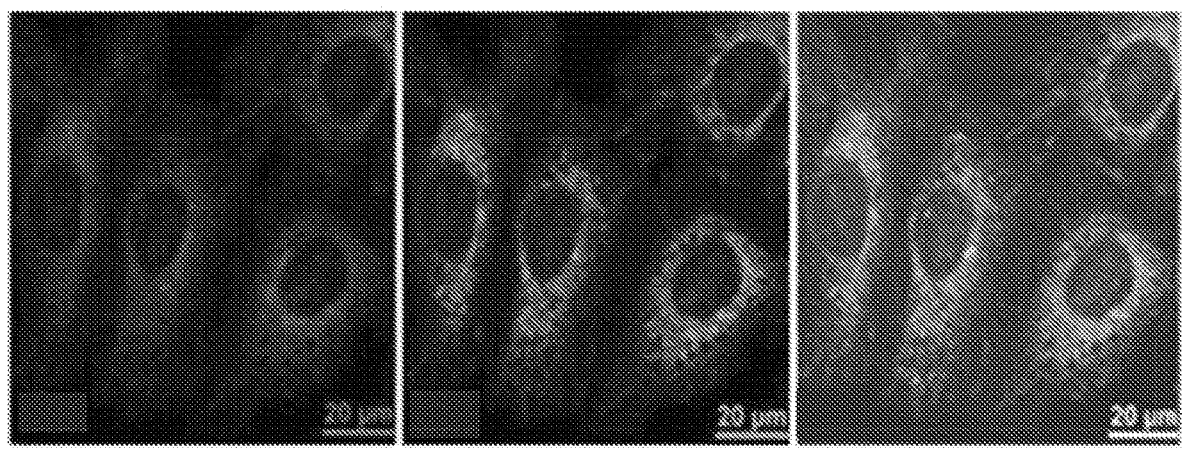
FIGS. 3A, 3B, 3C present fluorescence images, formed with the use of a confocal microscope, of KS6 (2 μM) in HeLa cells co-stained with MitoTracker® Green FM.
Figure 6B:
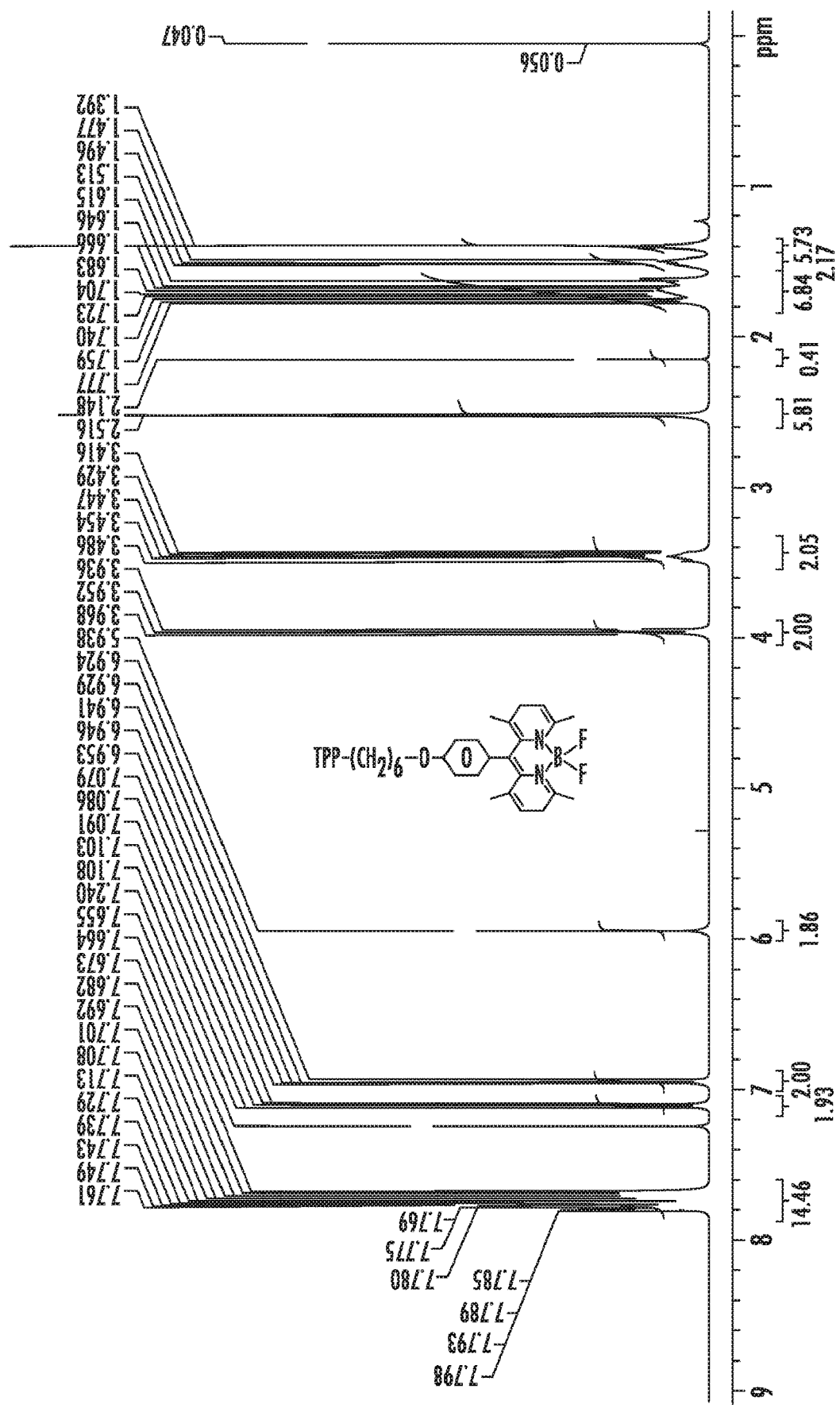
FIG. 6B illustrates an $^1$H NMR spectrum of compound 3 in $CDCl_3$.
Figure 6C:
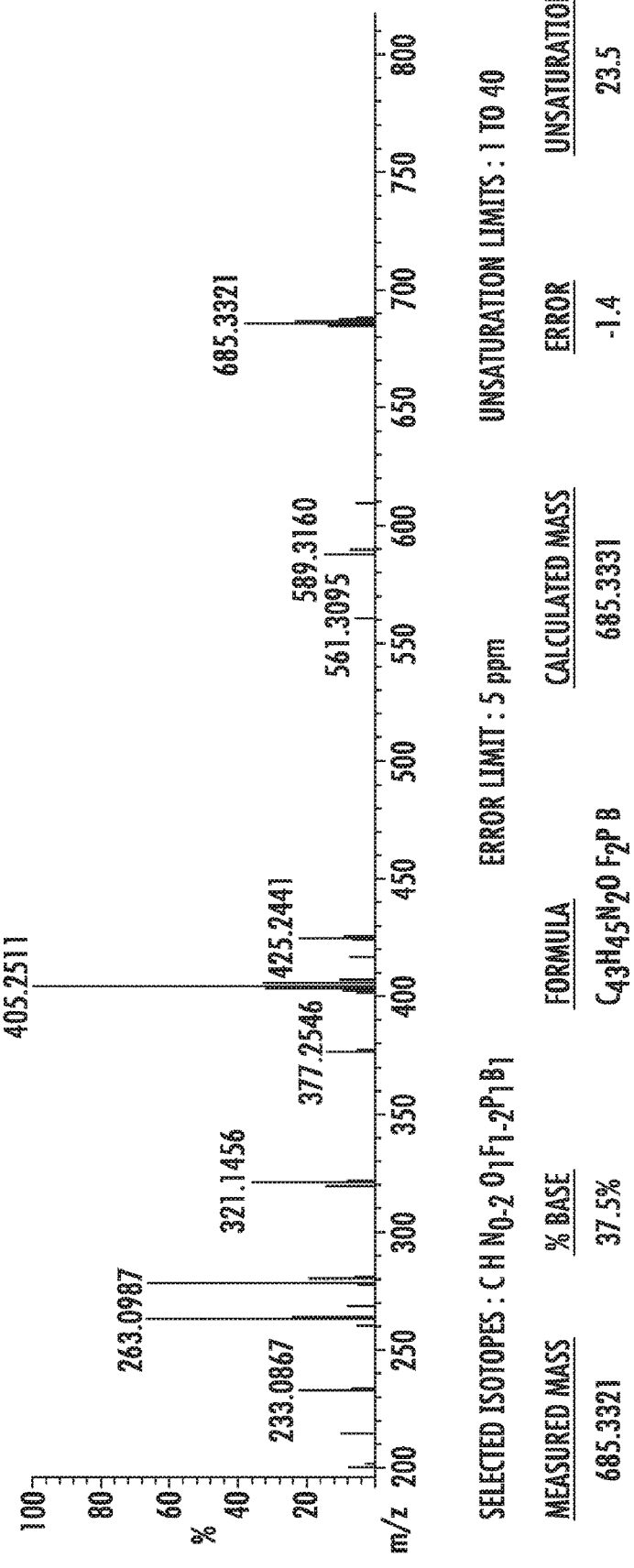
FIG. 6C shows a high resolution-mass spectrum (procured with the APCI ionization method) of compound 3.
Figure 6D:
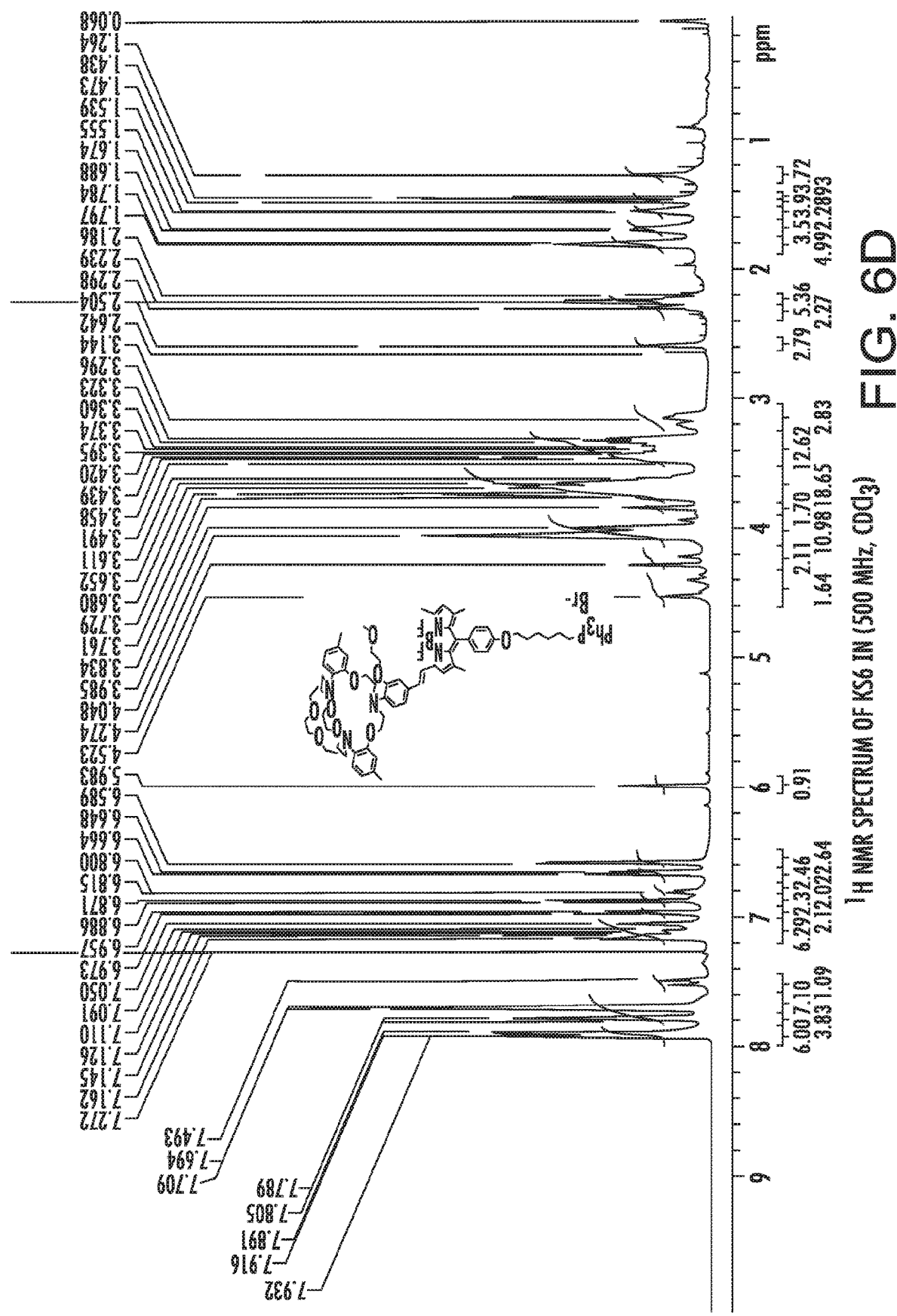
FIG. 6D illustrates an $^1$H NMR spectrum of KS6 in $CDCl_3$.
Figure 6E:
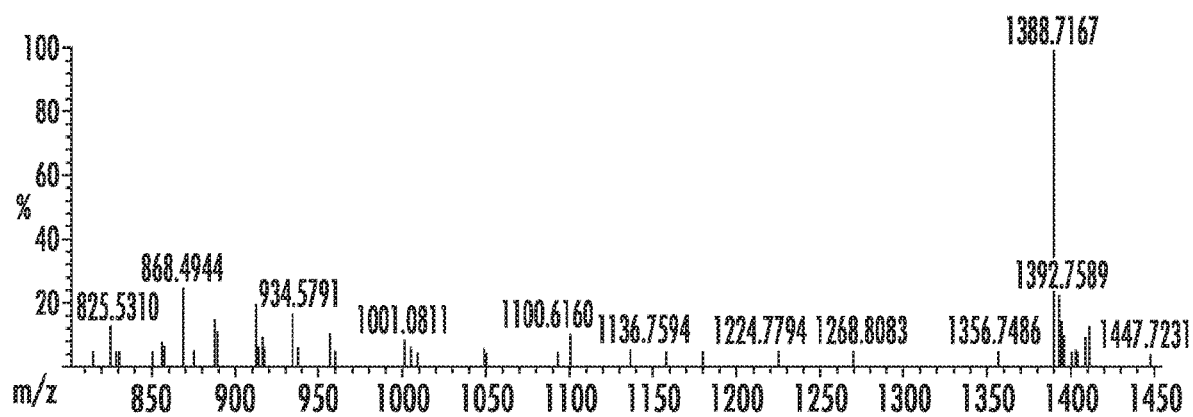
FIG. 6E presents a high resolution mass spectrum (acquired with the ESI ionization method) of KS6 (discussed below)
Figure 6E:
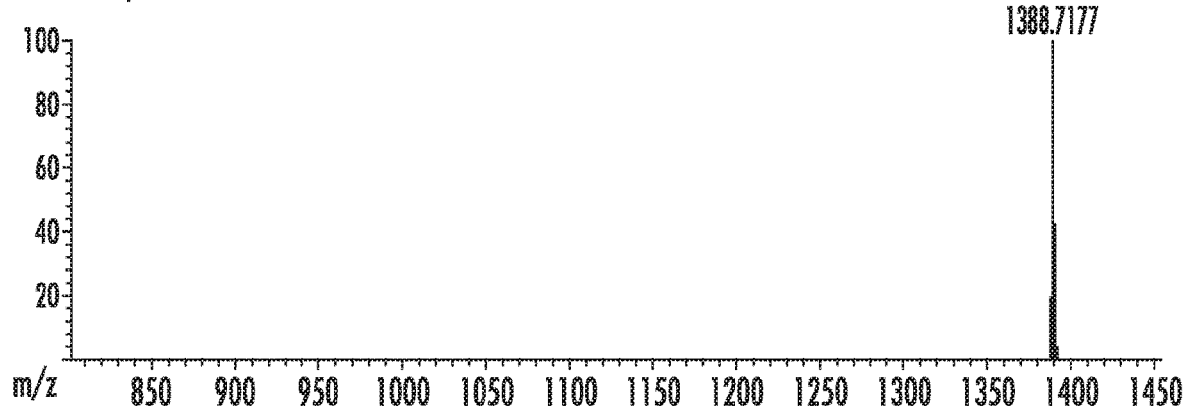
Figure 9:
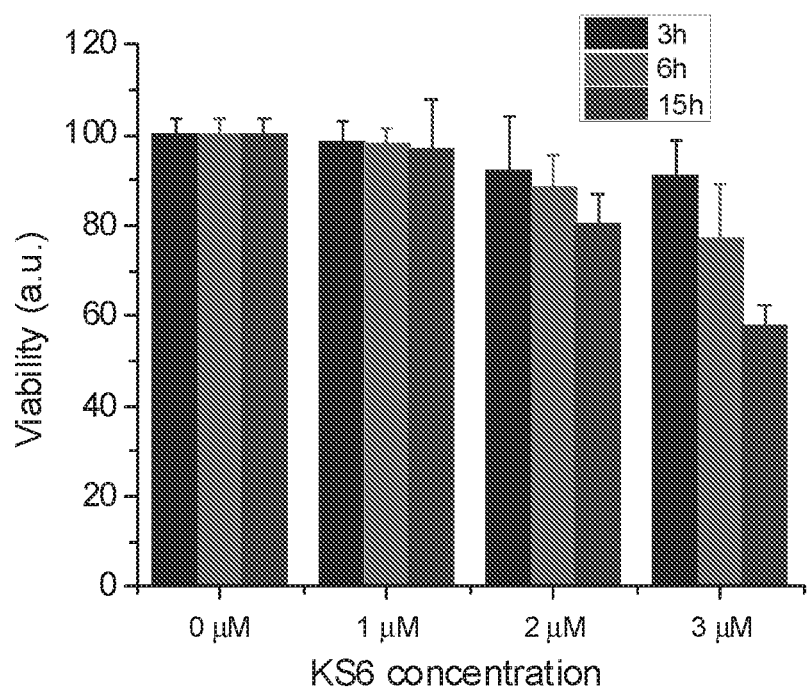
FIG. 9 shows the results of the cell viability test of HeLa cells, conducted using the MTT assay for KS6 at different concentrations and times.

Referring to FIGS. 3A through 3C, KS6 sensors were confirmed to mainly localize in mitochondria of cells and are suitable for cell imaging. The cytotoxicity of KS6 to human HeLa cells was investigated using MTT assay. At a concentration of 3 μM of KS6, more than 90% of the cells were viable after internalization of the sensor in cells for 3 h (FIG. 9). While at a lower concentration of 2 μM of KS6, more than 80% of the cells were viable after 15 h. In both cases, KS6 can be used for cell imaging due to its large absorption coefficient and high fluorescent quantum yield after binding K+ ion. A colocalization assay was carried out with mitochondrial dye MitoTracker® Green FM and KS6 in the HeLa cells (FIGS. 3A-3C). The Pearson's correlation coefficient and the Mander's overlap coefficient are 0.89 and 0.94, respectively, indicating that KS6 is predominantly localized in the mitochondria of live cells (K. W. Dunn, M. M. Kamocka, J. H. McDonald, *Am. J. Physiol. Cell Physiol.* 2011, 300, C723-C742).

Figure 10A:
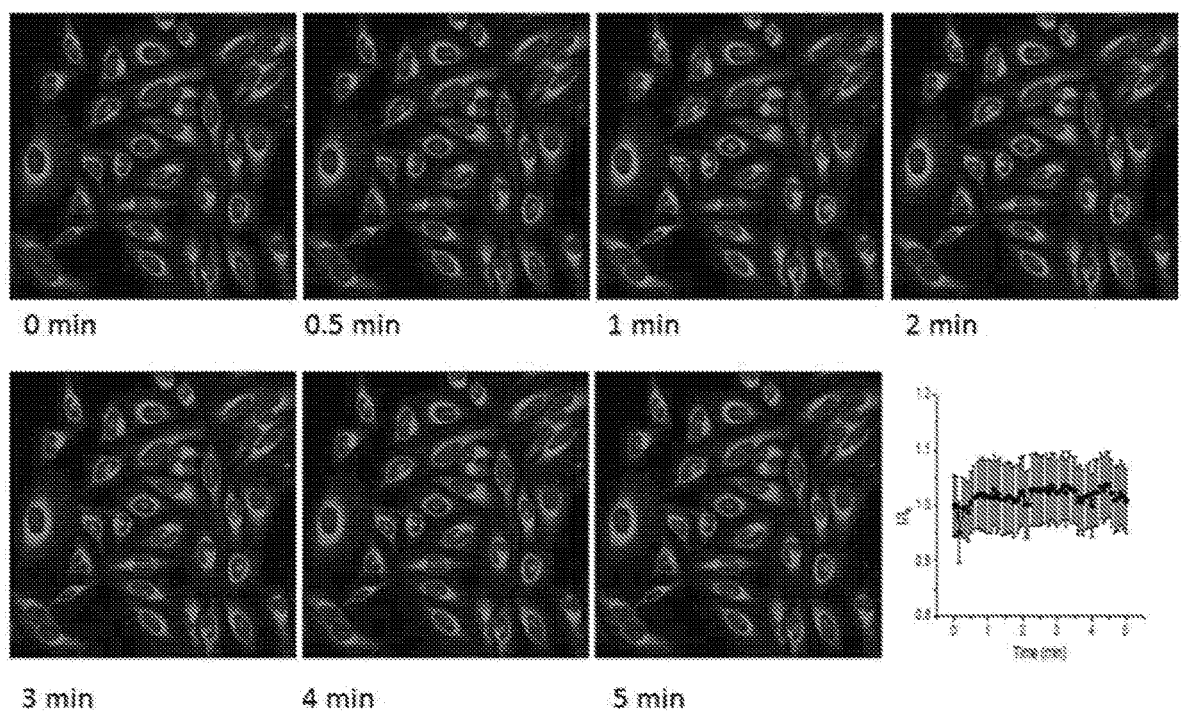
FIGS. 10A and 10B illustrate time-dependent fluorescence images of HeLa cells in EMEM containing 10 μM of ionomycin and 200 mM of KCl.
Figure 10B:
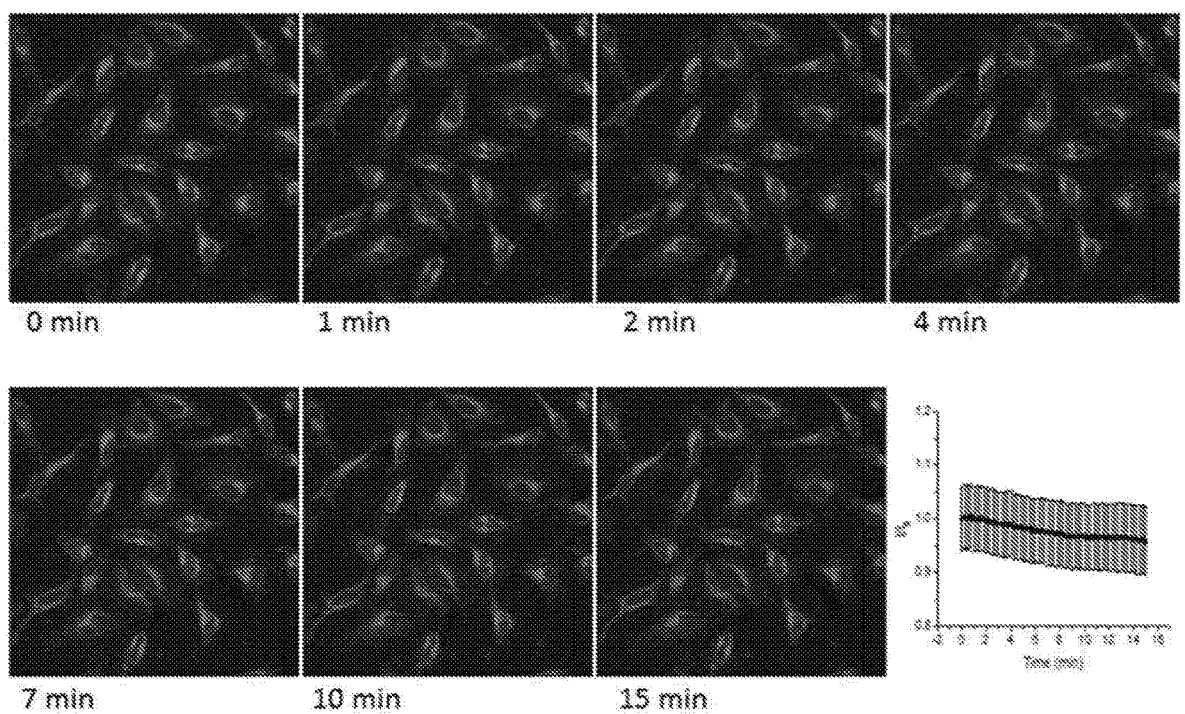

Referring to FIGS. 4A through 4F, 10A, 10B, 11, and 12, KS6 sensors were shown to be utilized to monitor influx and efflux of potassium ions in mitochondria. In certain embodiments, to monitor the mitochondrial K+ concentration change under stimulation, HeLa cells internalized with KS6 (2 μM) for 10 minutes were treated with an ionophore, ionomycin (10 μM) at 37° C. Fast efflux of mitochondrial K+ within 2 minutes was observed by the decrease of fluorescence intensity (FIGS. 4A through 4F). Control experiments without ionomycin stimulation showed no obvious fluorescence intensity change in culture medium containing either 20 or 200 mM KCl, respectively (FIGS. 10A and 10B).

Figure 11:
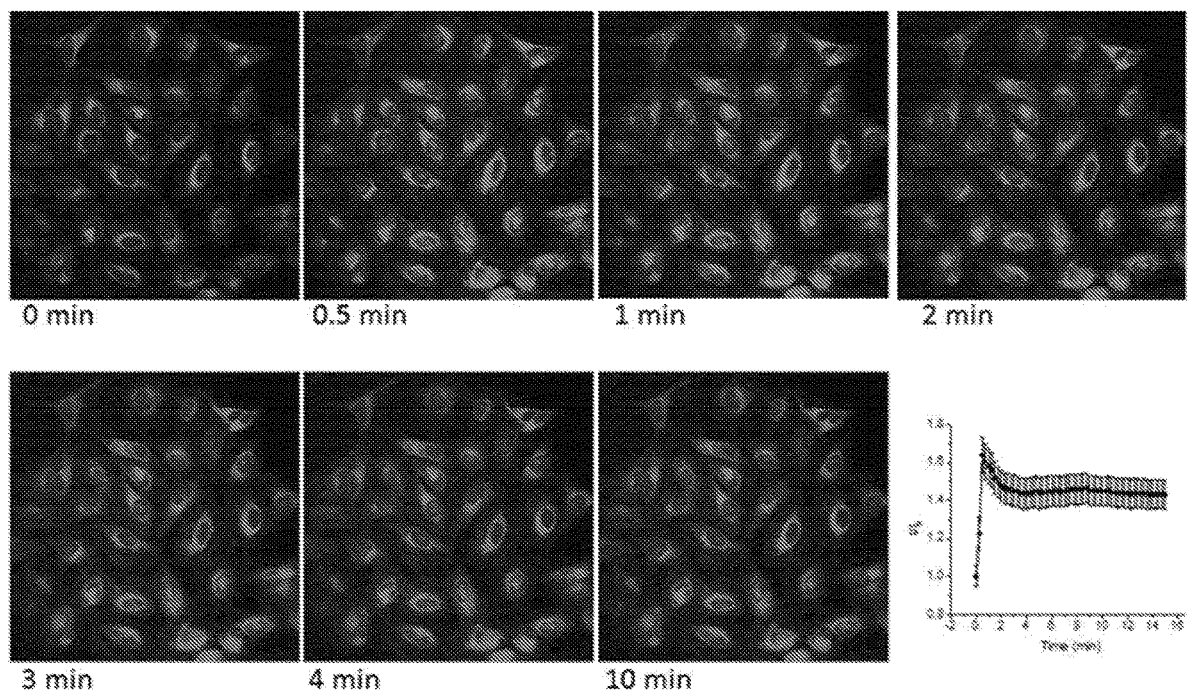
FIG. 11 shows time-dependent fluorescence images of HeLa cells in EMEM containing 20 mM of KCl after stimulation with nigericin (10 μM)

Further, in other embodiments, the influx and then efflux of K+ in mitochondria was observed in HeLa cells after stimulation with another ionophore, nigericin (10 μM), in a medium containing 200 mM of KCl (FIG. 11). Within a 30 second period of time, the average fluorescent intensity of cells increased by 60%, indicating the influx of K+ in mitochondria. After 2 minutes lapsed, potassium efflux from mitochondria was observed by the decrease of fluorescence intensity. The final intensity after stabilization for 10 minutes was 40% above that before stimulation by nigericin.

Figure 12:
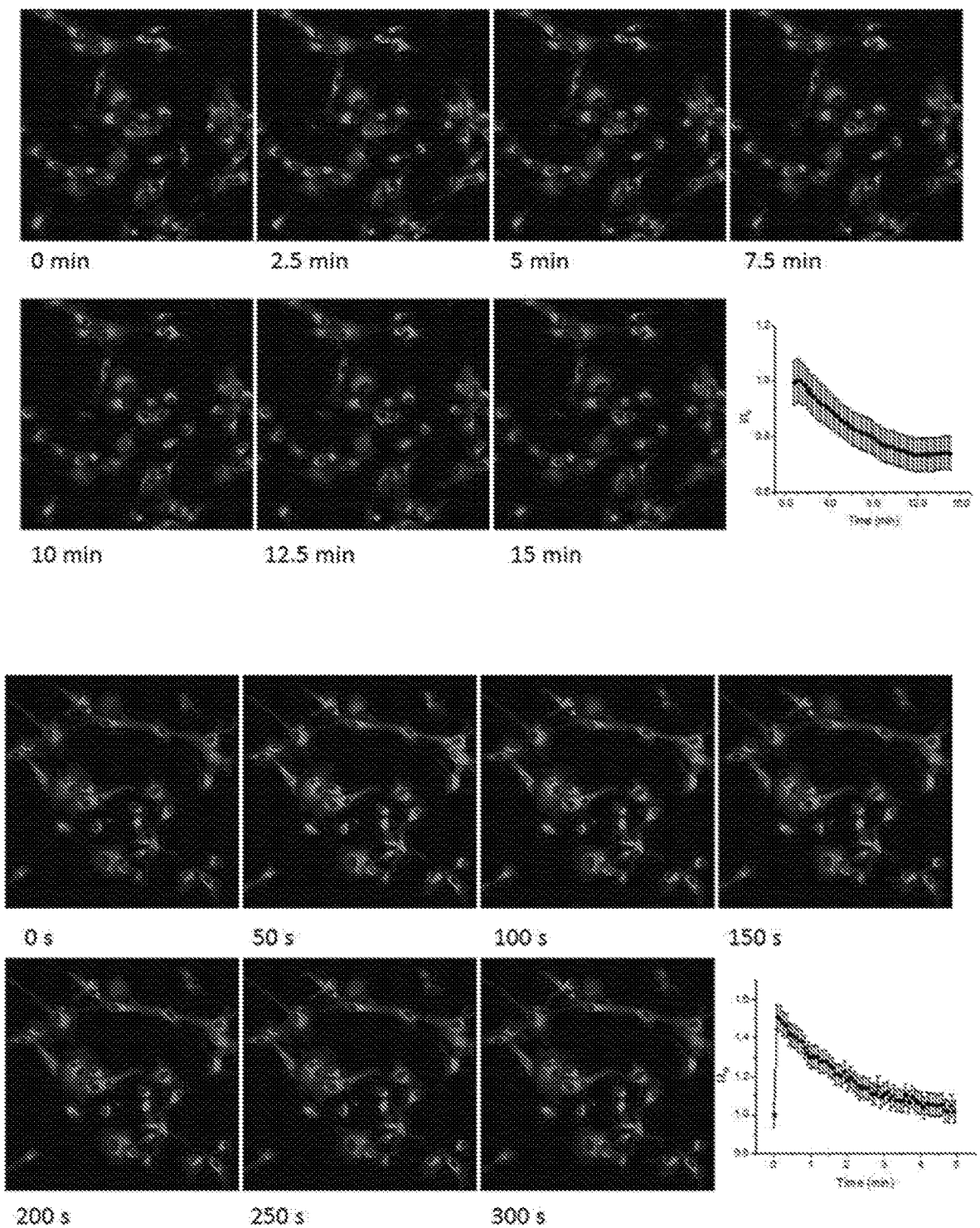
FIG. 12 illustrate time-dependent fluorescence images of U87MG cells in EMEM containing 20 mM of KCl (Top) and 200 mM of KCl (Bottom) without stimulation.
Figure 13:
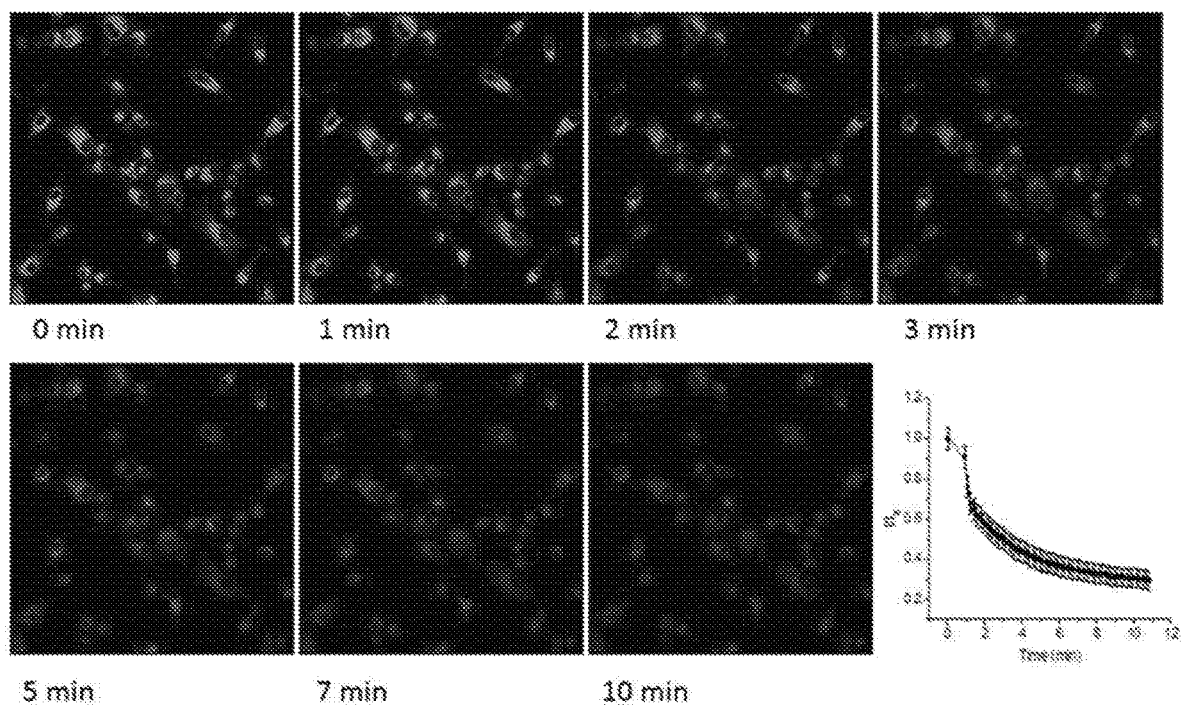
FIG. 13 shows time-dependent fluorescence images of U87MG Cells in EMEM containing 200 mM of KCl after stimulation with ionomycin (20 μM)

In addition, KS6 sensors were demonstrated to possess the ability to monitor the influx and then efflux of K+ in mitochondria in types of cells, which can physiologically act as a K+ buffer to remove excess potassium. In certain embodiments, referring to FIGS. 11 and 12, K+ influx/efflux in U87MG cells were investigated with/without stimulation. In comparison with HeLa cells, a simple treatment of U87MG cells with a medium containing 20 mM of KCl caused slow fluorescence intensity decrease to 74% in 12 minutes. When the concentration of KCl in the medium increased to 200 mM, the fluorescence intensity from U87MG cells first jumped 50% above that before the treatment, and slowly decreased to its original state (FIG. 12). Stimulating U87MG cells with ionomycin (10 μM) in medium caused a fluorescence intensity decrease to 59% from mitochondria within 2 minutes, and finally reached 30% of its original intensity in the end, indicating the K+ efflux from the mitochondria (FIG. 13).

Referring to FIGS. 5A through 5F, K+ influx/efflux was also observed when KS6 internalized U87MG cells were treated with nigericin (20 μM) in the presence of 200 mM of KCl. Within 30 seconds after the treatment, the fluorescence intensity of U87 cells increased by 250%. After reaching the fluorescence maximum, the fluorescence intensity started to decrease and decayed to 75% of the maximum value, indicating the efflux of K+ ions from mitochondria. The quick influx of the K+ ions in mitochondria might be caused by nigericin-facilitated diffusion of K+ ions into the mitochondrial under transmembrane potential.

Figure 14:
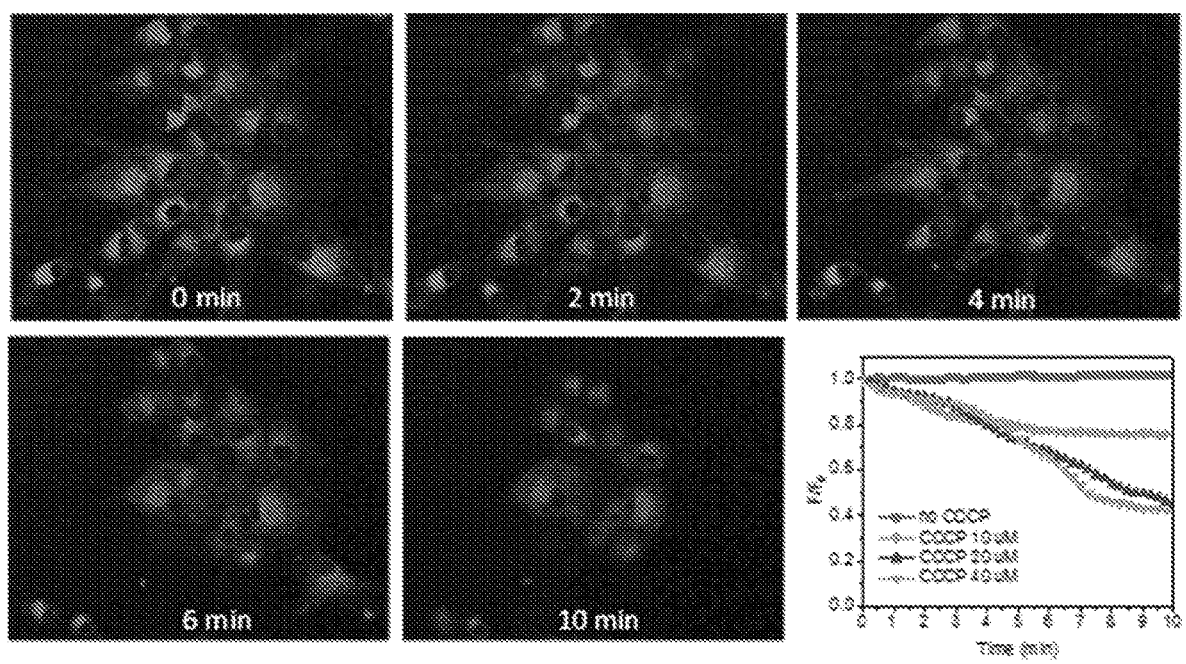
FIG. 14 shows typical time dependent fluorescence images of U87MG cells under the stimulation of 40 μM CCCP from 0 to 10 minutes. The plot at the right bottom shows the intensity ratio changes under different CCCP concentrations. $F_0$ is the average intensity at time of 0; F is the average intensity at various time.
Figure 15:
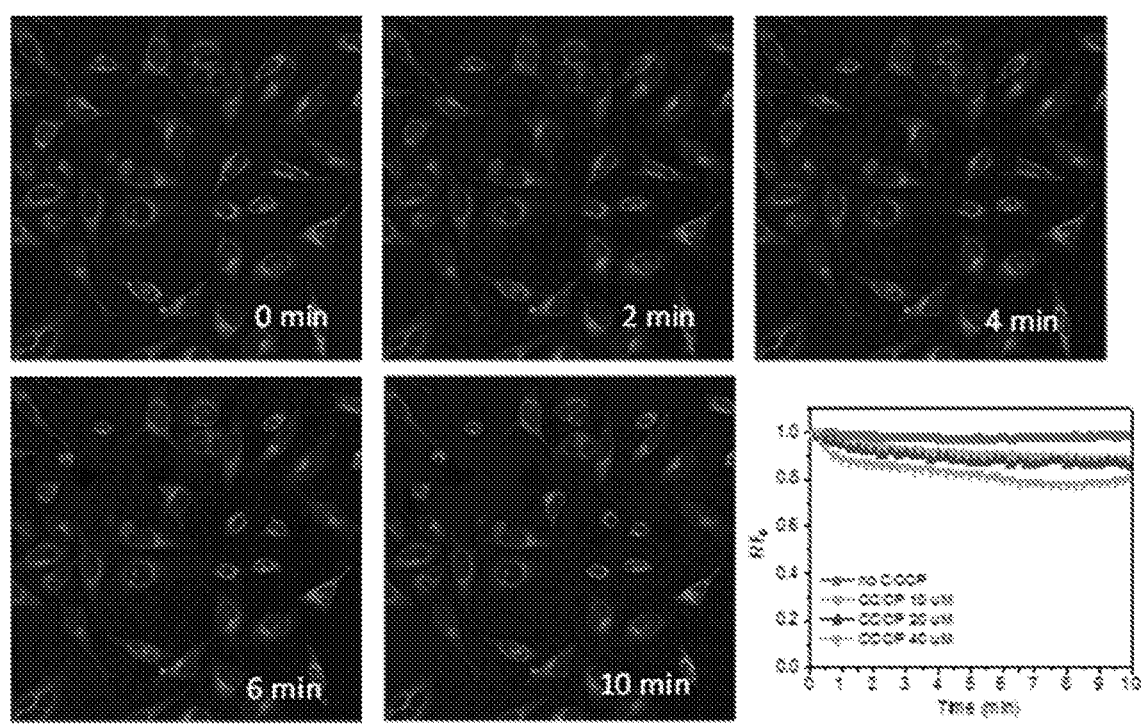
FIG. 15 illustrates typical time-dependent fluorescence images of HeLa cells under the stimulation of 40 μM CCCP from 0 to 10 minutes. The plot at the right bottom shows the intensity ratio changes under different CCCP concentrations. $F_0$ is the average intensity at time of 0; F is the average intensity at various times.

Another typical stimulator to study the ionic fluxes of mitochondria including potassium ions is carbonyl cyanide m-chlorophenylhydrazone (CCCP), which is one of OXPHOS uncouplers working as proton transmembrane carrier. Two cell lines, HeLa and U87MG, were used in this research to dynamically detect the potassium fluxes in mitochondrial matrix responding to membrane potential changes induced by CCCP. Cells were incubated with 1 μM of KS6 for 30 minutes before two concentrations, i.e. 10 μM and 40 μM, of CCCP were applied on these cells. No fluorescence intensity change was observed without the CCCP treatment; whereas, compared to control experiment (no CCCP treatment), fluorescence intensities of KS6 in mitochondria dropped about maximum 50% in U87MG cells and 20% in HeLa cells depending on CCCP concentrations, showing the different behaviors of various cell lines (FIGS. 14 and 15) to the stimulation.

After the characterization of the KS6 sensors, the following paragraphs describe the process of synthesizing KS6 sensors. In certain embodiments, compound 1 (4-(6-Bromohexyloxy)-benzaldehyde), having a structure:

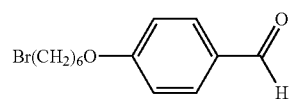

is used, according to an embodiment, to synthesize compound 2 ([6-(4-formylphenoxy)hexyl]triphenylphosphonium bromide) that has a structure:

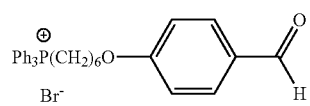

The synthesis scheme is shown below and further described in example 1.

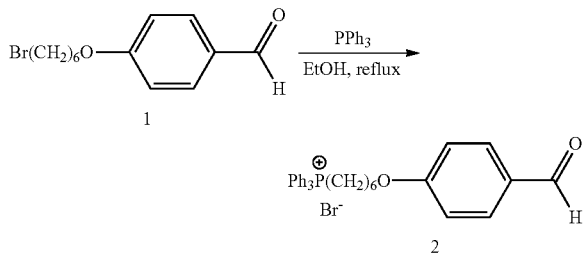

Compound 2 is prepared by reaction of compound 1 in the presence of any reagent which would achieve formation of compound 2. In certain embodiments, the reagent can be triphenylphosphine in ethanol.

The TPP+-containing BODIPY (compound 3), having a structure:

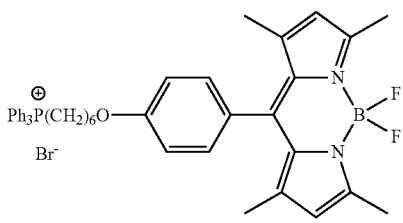

is also disclosed. Compound 3 is prepared by reaction of 2 with any reagent that would achieve formation of compound 3, in the presence of any catalysts that would achieve catalyzing formation of compound 3, followed by oxidation with any reagents that would achieve oxidation in this process, and treated with $BF_3 \cdot OEt_2$ and triethylamine. In certain embodiments, reagent 2,4-dimethylpyrrole is used herein, trifluoroacetic acid in

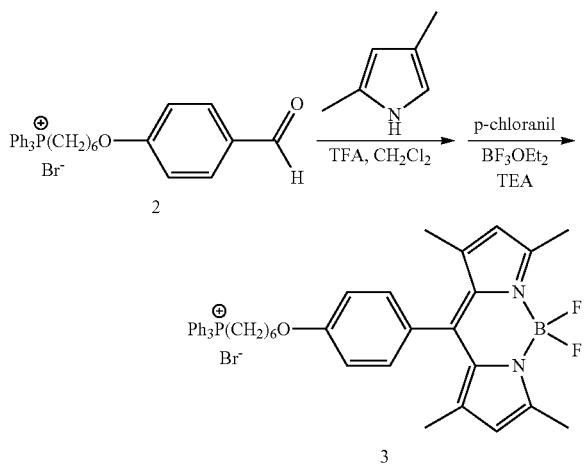

anhydrous dichloromethane is used to catalyze, and p-chloranil is used to oxidize the reaction. The synthesis scheme is shown below and further described in example 1.

KS6 is obtained by condensation of compound 3 with TAC-CHO, which has a structure:

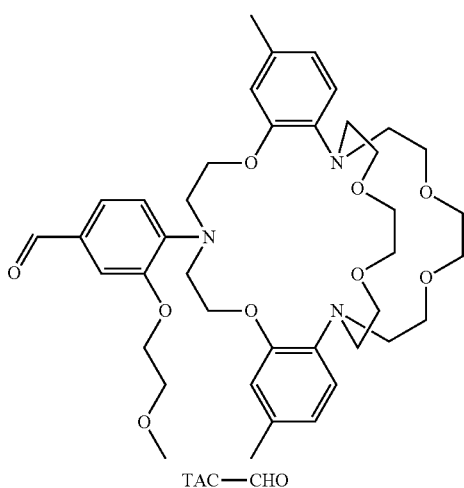

in any reagent that would achieve formation of KS6 using any catalysts that would achieve catalyzing formation of KS6. In certain embodiments, reagent benzene is used herein and piperidinium acetate is used as the catalyst. In other embodiments, reagent toluene is used instead of benzene.

EXAMPLES

Example 1—Synthesis of KS6

Synthesis of [6-(4-formylphenoxy)hexyl]triphenylphosphonium bromide (2): 4-(6-Bromohexyloxy)-benzaldehyde (2.85 g, 10 mmol) and triphenylphosphine (2.62 g, 10 mmol) were added into a flask containing 30 mL of ethanol. The mixture was refluxed for 24 h. After removal of solvent by vacuum rotavapor, the remaining solid was purified by silica flash column chromatography with gradient solvent from $CH_2Cl_2$ to $CH_2Cl_2$/MeOH (v/v=9/1). 3.83 g of white solid was obtained, yield: 70%. $^1$H NMR (CDCl$_3$, δ) (ppm): 9.84 (s, 1H, CHO), 7.88-7.79 (m, 6H, Ar—H), 7.76-7.66 (m, 5H, Ar—H), 7.68 (m, 6H, Ar—H), 6.93 (2H, Ar—H), 4.00 (t, 2H, CH$_2$O), 3.91 (t, 2H; CH$_2$), 1.75 (m, 4H), 1.64 (m, 2H), 1.48 (m, 2H).

Synthesis of 4-[6-(triphenylphosphonium)hexyloxy]phenyl-1,3,5,7-tetramethyl borondipyrro-methene bromide (3): [6-(4-formylphenoxy)hexyl]triphenylphosphonium bromide (2, 1.1 g; 2 mmol) and 2,4-dimethylpyrrole (0.52 mL; 5 mmol) were added in a dry 500 mL three-neck flask under nitrogen. 200 mL of anhydrous dichloromethane was added, followed by 2 drops of trifluoroacetic acid. After the mixture was stirred at room temperature for 12 hours, p-chloranil (0.487 g, 2 mmol) in 100 mL dichloromethane was added. After stirred for another 30 minutes, 10 mL of trimethylamine and 10 mL of $BF_3OEt_2$ was added in. The mixture was poured into 200 mL of water, and afterwards stirred for another 2 hours. The dark organic phase was separated using separation funnel, and washed with HCl (1.0 M), water, 10% $Na_2CO_3$ aqueous solution, and then water. The organic phase was removed under vacuum. The final product was purified by silica flash chromatography using $CH_2Cl_2$ to $CH_2Cl_2$/MeOH (v/v: 95:5) as eluent; 0.60 g of product was obtained. Yield: 39%. $^1$H NMR (CDCl$_3$, δ) (ppm): 7.80-7.70 (m, 15H, Ph$_3$P$^+$), 7.10-7.09 (dd, 2H, AR-H), 6.96 (d, 2H, AR-H, J=8.4 Hz), 5.95 (s, 2H, C—H); 3.97 (t, 2H, CH$_2$), 3.36 (m, 2H, CH$_2$), 2.53 (s, 6H, 2×CH$_3$), 1.78 (m, 2H, CH$_2$), 1.69 (m, 4H, 2×CH$_2$), 1.54 (m, 2H, CH$_2$), 1.41 (m, 6H, 2×CH$_3$). $^{13}$C NMR (100 MHz, CDCl$_3$) δ (ppm): 159.62, 155.12, 143.20, 142.01, 135.08, 135.05, 133.52, 133.42, 131.85, 130.58, 130.45, 129.10, 126.77, 121.03, 118.70, 117.84, 115.04, 67.83, 30.07, 29.91, 28.89, 25.53, 22.60, 22.55, 22.15, 21.65, 14.59, 14.54. HRMS (APCI) (m/e): calculated for $C_{43}H_{45}N_2OF_2PB$: 685.3331; found: 685.3321.

Synthesis of KS6.

TAC-CHO (72.0 mg, 0.1 mmol) and compound 3 (76.6 mg, 0.1 mmol) were refluxed in a mixture of benzene (5 mL), acetic acid (30 μL) and piperidine (36 μL) overnight. The reaction mixture was cooled to room temperature, diluted with 10 mL $CH_2Cl_2$ and washed with water. The organic layer was dried over anhydrous $Na_2SO_4$, filtered and evaporated. KS6 (27 mg) was obtained by silica flash chromatography using $CH_2Cl_2$ to $CH_2Cl_2$/MeOH (v/v: 95:5) as eluent. Yield: 18.4%. KS6 was further purified by reverse-phase HPLC using water and methanol/acetic acid (0.1%) for NMR and Mass spectra characterization. $^1$H NMR (CDCl$_3$, δ) (ppm): 7.88-7.67 (m, 15H, PPh$_3$), 7.6-6.45 (m, 15H, Ar—H and vinyl-H), 5.95 (s, 1H), 4.2-3.2 (m, 43H), 2.56 (s, 3H, CH$_3$); 2.10 (s, 6H, 2×CH$_3$Ph); 1.78-1.60 (m, 6H, 3×CH$_2$); 1.54 (m, 8H, CH$_2$, 2×CH$_3$). HRMS (ESI, m/e): calculated for C$_{83}$H$_{98}$BF$_2$N$_5$O$_9$P$^+$: 1388.7177; found 1388.7167.

Example 2—Ionic Fluxes of Mitochondria

Carbonyl cyanide m-chlorophenylhydrazone (CCCP), which is one of OXPHOS uncouplers working as proton transmembrane carrier, is used as a typical stimulator to study the ionic fluxes of mitochondria including potassium ions. Two cell lines, HeLa and U87MG, were used in this research to dynamically detect the potassium fluxes in mitochondrial matrix responding to membrane potential changes induced by CCCP. Cells were incubated with 1 μM of KS6 for 30 minutes before two concentrations, i.e. 10 μM and 40 μM, of CCCP were applied on these cells. No fluorescence intensity change was observed without the CCCP treatment; whereas, compared to control experiment (no CCCP treatment), fluorescence intensities of KS6 in mitochondria dropped about maximum 50% in U87MG cells and 20% in HeLa cells depending on CCCP concentrations, showing the different behaviors of various cell lines to the stimulation.

Materials and Methods

Reagents.

All mentioned chemicals were used without additional purification. MitoTracker® Green FM was ordered from Life technology (Carlsbad, Calif.). 4-(6-Bromohexyloxy)-benzaldehyde (1) and TAC-CHO were synthesized according to known procedures, respectively.

Instruments.

A Varian liquid-state NMR operated at 400 MHz was used for $^1$H NMR spectra measurements. High resolution Mass Spectra of the intermediates and the final product were obtained by Joel LCmate at CLAS High resolution Mass Spectrometry Lab, ASU, using either atmospheric pressure chemical ionization (APCI) or electrospray ionization (ESI) methods. A Shimadzu UV-3600 UV-Vis-NIR spectrophotometer (Shimadzu Scientific Instruments, Columbia, Md.) was used for UV-Vis absorption spectra measurements. A Shimadzu RF-5301 spectrofluorophotometer was used for fluorescence measurements.

Fluorescence Quantum Efficiency Determination.

The fluorescence quantum yields ($\phi_f$) of samples in solution were measured by using Rhodamine 101 in ethanol ($\phi_f$=100%) as a standard excited at 540 nm and were calculated according to the following equation:

$$\phi_s = \phi_r \left(\frac{A_r}{A_s}\right)\left(\frac{I_s}{I_r}\right)\left(\frac{n_s^2}{n_r^2}\right) \quad (1)$$

where $\phi_s$ and $\phi_r$ are the fluorescence quantum yields of standards and the samples, respectively. $A_r$ and $A_s$ are the absorbance of the standards and the measured samples at the excitation wavelength (adjusting the concentration of both the reference and the sample to make $A_r$ and $A_s$ around 0.05), respectively. $I_r$ and $I_s$ are the integration emission intensities of the standards and samples, respectively. $n_r$ and $n_s$ are the refractive indices of the corresponding solvents of the solutions, respectively.

Sensor Titration with KCl in a Surfactant Solution Containing:

A). CTAB surfactant: 10 μL of KS6 dissolved in DMSO (1 mM) was added into a solution containing 1 mL of Tris-HCl (10 mM, pH 7.4) buffer solution and 1 mL of CTAB (1 mM) in water. This resulted in the final KS6 concentration of 5 μM in the solution. Different volumes of KCl (4.0 M) were added into the solution. The mixture was gently shaken for 10 seconds. Both UV-Vis spectra and fluorescence spectra were recorded to study KS6's responses to [K$^+$]. KS6/metal ion complexes were excited at 540 nm and emission spectra were collected from 550 to 750 nm. The real concentration of the K$^+$ was calculated after volume correction.

B). Pluronic F127. 10 μL of KS6 dissolved in DMSO (1 mM) and 20 μL of Pluronic F127 (10%) in DMSO were added into a solution containing 1 mL of Tris-HCl (10 mM, pH 7.4) buffer and 1 mL of DI water. This resulted in the final KS6 concentration to be 5 μM in the buffer solution. Similar titration was performed as described with CTAB surfactant.

C). Sodium dodecyl sulfate (SDS): 10 μL of KS6 dissolved in DMSO (1 mM) was added into a solution containing 1 mL of Tris-HCl (10 mM, pH 7.4) buffer and 1 mL of 5 mM of SDS in DI water. Titration with KCl (4.0 M) in water caused formation of white precipitate.

Cell Culture for Imaging.

U87MG cells (American Type Culture Collection, ATCC, Manassas, Va.) were cultured in Eagle's minimum essential medium (EMEM) supplemented with 10% fetal bovine serum, 100 u/mL penicillin, and incubated at 37° C. in 5% CO$_2$ atmosphere. Cells were then seeded onto 96 well plates at 10,000 cells per well, and incubated overnight at 37° C. The sensor dissolved in DMSO was added to the medium to make the sensor concentrations in a range of 0.5-5 μM. 10 min of internalization was found to be sufficient for achieving satisfactory images. To achieve images with satisfactory signal-to-noise ratio, a sensor concentration of 2 μM was usually used for intracellular study.

Colocalization Test of KS6 and MitoTracker® Green FM:

Cells were co-stained using the sensor KS6 in combination with MitoTracker® Green FM. To co-stain the mitochondria, MitoTracker® Green FM in DMSO was used. Cells were first internalized with KS6 (2 μM in cell culture medium) for 10 minutes. MitoTracker® Green FM diluted in the fresh medium was then added into the wells to stain cell for 10 min at 37° C. The resulting concentration of MitoTracker® Green FM in the cell medium was 50 nM.

Under a Nikon C2Si Eclipse Ti confocal fluorescence microscope (Melville, N.Y.), Sensor (KS6) was excited at 561 nm and its red emission was collected using a 605/75 nm filter set. MitoTracker® Green FM was excited at 488 nm and its green emission was collected using a 515/30 nm filter set.

Monitoring the Intracellular K$^+$ Efflux Using KS6.

HeLa cells or U87MG cells were seeded onto 96 well plates with 5,000 cells and 15,000 cells per well respectively in 100 μL medium, and incubated overnight at 37° C. On the following day, the cells were internalized with KS6 (2 μM) for 10 min at 37° C. A nigericin solution was then added. Final concentrations of nigericin in the cell culture medium were 10 μM. Fluorescence in cells was visualized by Nikon C2Si Eclipse Ti confocal fluorescence microscope (Melville, N.Y.) at 37° C.

Cytotoxicity of KS6 to Cells by Viable Cell Counts Using MTT.

To determine cell viability, a colorimetric MTT metabolic activity assay was used. HeLa cells ($1\times10^4$ cells/well) were cultured in a 96-well plate at 37° C., and exposed to varying concentrations of KS6 for 3, 6, and 15 hours. Cells treated with medium only served as a negative control group. After removing the supernatant of each well and washing by PBS, 15 µL of MTT solution and 100 µL of medium were then introduced. After incubation for another 4 hours, the resultant formazan crystals were dissolved in solubilization solution (100 µL) and the absorbance intensity measured by a microplate reader (BioTek Synergy H4, USA) at 570 nm. All experiments were performed in triplicate, and the relative cell viability (%) was expressed as a percentage relative to the untreated control cells.

RESULTS AND DISCUSSION

The demonstrated KS6 is a predominantly mitochondria-targeting $K^+$ sensor, that selectively responds to $K^+$ with a 130-fold fluorescence enhancement, (at a $K^+$ concentration of 0.8 M) and a dynamic $K^+$ ion concentration range (30-500 mM). The KS6 is able to localize into the mitochondria, making it the first mitochondria-specific potassium ion sensor. During the use of this sensor, it was demonstrated that KS6 is a useful tool to monitor mitochondria potassium fluxes (both influx and efflux) under various stimulations, although not quantitatively yet.

While the technology is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the technology should not be viewed as being limited to the disclosed embodiment(s).

What is claimed is:

1. A potassium-sensing compound, comprising a sensing range of potassium ion concentration from about 30 mM to about 500 mM potassium, of formula (I):

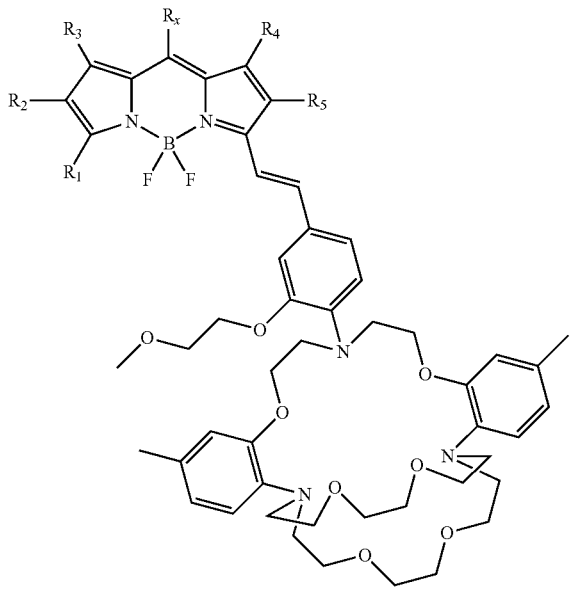

(I)

or a salt form thereof, wherein:

$R_1$, $R_3$, $R_4$ in formula (I) are independently selected from the group consisting of H, $CH_3$, and $CH_2CH_3$;

$R_2$, $R_5$ in formula (I) are independently selected from the group consisting of H, $CH_3$, $CH_2CH_3$, $CO_2H$, $CO_2CH_3$, $CO_2Et$, $CH_2CH_2COOCH_3$, $CH_2CH_2COOCH_2CH_3$, $CH_2CH_2COOH$, and 2-thiophene; and $R_x$ in formula (I) is selected from the group consisting of

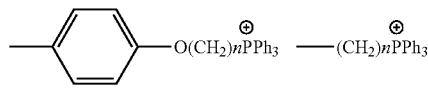

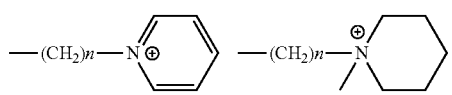

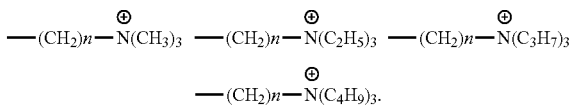

2. The compound of claim 1, further configured to target a plurality of potassium channels (Kch) in mitochondria.

3. The compound of claim 1, wherein $R_x$ is

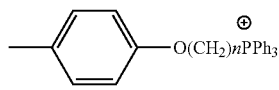

and each of $R_1$, $R_2$, $R_3$, $R_4$, and $R_5$ is H, and wherein n is an integer greater than zero.

4. The compound of claim 3, configured to increase fluorescence intensity 130-fold when exposed to potassium ions at a concentration of about 0.8 M relative to fluorescence intensity when exposed to a test solution containing no potassium.

5. The compound of claim 3, wherein the fluorescence intensity of said compound increases 1.3 fold at a wavelength of light of about 572 nm when said compound is exposed to a concentration of potassium at about 5 mM, and increases 57 fold at a wavelength of light of about 572 nm when said compound is exposed to a concentration of potassium at about 150 mM, each relative to fluorescence intensity when exposed to a test solution containing no potassium.

6. The compound of claim 3, wherein the fluorescence intensity is independent from a pH value of a cellular environment within a range from about 5.5 to about 9.0.

7. The compound of claim 3, wherein the fluorescence intensity is independent from an auxiliary ion, wherein the auxiliary ion is selected from a group consisting of $Na^+$, $Ca^{2+}$, $Mg^{2+}$, $Fe^{3+}$, $Fe^{2+}$, $Zn^{2+}$, $Mn^{2+}$, and $Cu^{2+}$, at a concentration from about 50 µM to about 15 mM.

8. The compound of claim 7, wherein the fluorescence intensity is further independent from $H_2O_2$ at about 100 nM.

9. A method of synthesizing the compound formula (II):

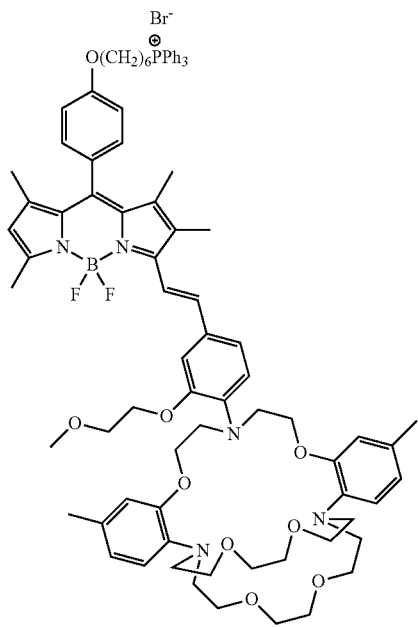

II the method comprising:

mixing 4-(6-Bromohexyloxy)-benzaldehyde and triphenylphosphine to obtain a first solid;

mixing the first solid and 2,4-dimethylpyrrole under nitrogen to obtain a first mixture;

adding dichloromethane and trifluoroacetic acid to the first mixture to obtain a second mixture;

stirring the second mixture at room temperature;

adding p-chloranil, trimethylamine, and boron trifluoride diethyl etherate (BF$_3$OEt$_2$) to the second mixture to obtain a third mixture;

separating an organic phase from the third mixture to obtain a second solid;

refluxing the second solid with TAC-CHO in a fourth mixture of benzene, acetic acid, and piperidine to obtain a fifth mixture; and separating an organic layer of the fifth mixture to obtain said compound.

* * * * *